US 9,770,581 B2

(12) United States Patent
Gerst et al.

(10) Patent No.: US 9,770,581 B2
(45) Date of Patent: Sep. 26, 2017

(54) ASEPTIC COUPLING DEVICES

(71) Applicant: Colder Products Company, St. Paul, MN (US)

(72) Inventors: Patrick Thomas Gerst, Oakdale, MN (US); Randall Scott Williams, Minneapolis, MN (US)

(73) Assignee: Colder Products Company, St. Paul, MN (US)

( * ) Notice: Subject to any disclaimer, the term of this patent is extended or adjusted under 35 U.S.C. 154(b) by 117 days.

(21) Appl. No.: 14/336,178

(22) Filed: Jul. 21, 2014

(65) Prior Publication Data
US 2015/0028586 A1    Jan. 29, 2015

Related U.S. Application Data

(60) Provisional application No. 61/857,471, filed on Jul. 23, 2013.

(51) Int. Cl.
| F16L 35/00 | (2006.01) |
| A61M 39/18 | (2006.01) |
| F16L 37/30 | (2006.01) |
| A61M 39/10 | (2006.01) |
| F16L 37/113 | (2006.01) |
| A61M 39/16 | (2006.01) |

(52) U.S. Cl.
CPC ........ *A61M 39/18* (2013.01); *A61M 39/1011* (2013.01); *F16L 37/113* (2013.01); *F16L 37/30* (2013.01); *A61M 39/165* (2013.01); *A61M 2039/1033* (2013.01); *A61M 2039/1044* (2013.01); *F16L 2201/10* (2013.01); *F16L 2201/44* (2013.01)

(58) Field of Classification Search
CPC  A61M 39/18; A61M 39/1011; A61M 39/165; A61M 2039/1033; A61M 2039/1044; F16L 37/113; F16L 37/30; F16L 2201/10; F16L 2201/44
USPC .......................... 285/3, 81, 38, 70, 423, 915
See application file for complete search history.

(56) References Cited

U.S. PATENT DOCUMENTS

| 3,865,411 A | 2/1975 | Rowe et al. |
| 3,900,223 A | 8/1975 | Schafer et al. |
| 3,909,910 A * | 10/1975 | Rowe .................... A61M 39/14 137/15.09 |

(Continued)

FOREIGN PATENT DOCUMENTS

| AU | 734259 B2 | 6/2001 |
| DE | 24 27 381 A1 | 7/1975 |

(Continued)

OTHER PUBLICATIONS

International Search Report and Written Report for PCT/US2010/027311 dated Aug. 6, 2010.

(Continued)

*Primary Examiner* — Basil Katcheves
*Assistant Examiner* — Joshua Ihezie
(74) *Attorney, Agent, or Firm* — Fish & Richardson P.C.

(57) ABSTRACT

An aseptic coupling device includes: a main body defining a front face; a membrane coupled to the front face, the membrane including a first portion coupled to the front face and a second portion folded over on the first portion; and a low friction member positioned between the first and second portions of the membrane.

19 Claims, 40 Drawing Sheets

(56) References Cited

U.S. PATENT DOCUMENTS

| | | | |
|---|---|---|---|
| 4,019,512 A * | 4/1977 | Tenczar | A61M 39/14 222/80 |
| 4,022,496 A | 5/1977 | Crissy et al. | |
| 4,187,846 A * | 2/1980 | Lolachi | A61M 39/14 285/3 |
| 4,418,945 A * | 12/1983 | Kellogg | A61M 39/14 285/423 |
| 5,492,147 A | 2/1996 | Challender et al. | |
| 5,810,398 A * | 9/1998 | Matkovich | A61M 39/1011 285/3 |
| 6,679,529 B2 | 1/2004 | Johnson et al. | |
| 7,523,918 B2 | 4/2009 | Matkovich et al. | |
| 7,918,243 B2 | 4/2011 | Diodati et al. | |
| 8,322,754 B2 * | 12/2012 | Carcagno | C09D 163/00 252/387 |
| 8,491,016 B2 * | 7/2013 | Williams | F16L 37/30 285/352 |
| 2002/0093192 A1 * | 7/2002 | Matkovich | A61M 39/1011 285/3 |
| 2003/0030272 A1 * | 2/2003 | Johnson | A61M 39/18 285/3 |
| 2003/0159764 A1 * | 8/2003 | Goto | C23C 24/08 148/519 |
| 2006/0192165 A1 | 8/2006 | Matkovich et al. | |
| 2009/0050213 A1 | 2/2009 | Biddell et al. | |
| 2009/0232586 A1 | 9/2009 | Diodati et al. | |
| 2010/0230950 A1 * | 9/2010 | Williams | F16L 37/30 285/38 |
| 2010/0230961 A1 | 9/2010 | Johnson | |
| 2013/0048111 A1 * | 2/2013 | Gebauer | A61M 39/162 137/544 |
| 2013/0200607 A1 | 8/2013 | Rodenberg et al. | |
| 2013/0207380 A1 * | 8/2013 | Williams | A61M 39/18 285/81 |
| 2013/0289517 A1 * | 10/2013 | Williams | F16L 37/098 604/500 |

FOREIGN PATENT DOCUMENTS

| | | |
|---|---|---|
| EP | 2 428 718 A2 | 3/2012 |
| WO | 2006/117138 A1 | 11/2006 |

OTHER PUBLICATIONS

International Search Report and Written Opinion for PCT/US2013/026374 dated Jul. 8, 2013.

International Search Report and Written Opinion for PCT/US2014/047413 dated Sep. 22, 2014.

* cited by examiner

ASEPTIC COUPLING DEVICES

BACKGROUND

Aseptic coupling devices can be used to connect two or more sterilized pathways. For example, aseptic coupling devices can be used to couple a fluid pathway from a first piece of processing equipment or container to a fluid pathway from a second piece of processing equipment or container to establish a sterile pathway for fluid transfer therebetween. Typical aseptic coupling devices require a "dry-to-dry" or "dry connection" that is created using one or more pathway clamping devices placed upstream of the aseptic coupling devices so that the aseptic coupling devices are kept free of fluid while the connection between the aseptic coupling devices is made. Once the sterile connection between the aseptic coupling devices is made, the clamping devices are removed to allow fluid to flow through the aseptic coupling devices.

SUMMARY

This disclosure relates to aseptic coupling devices and aseptic coupling arrangements. In accordance with the disclosure, a first aseptic coupling device for coupling to a second aseptic coupling device is provided.

In one aspect, an aseptic coupling device includes: a main body defining a front face; a membrane coupled to the front face, the membrane including a first portion coupled to the front face and a second portion folded over on the first portion; and a low friction member positioned between the first and second portions of the membrane.

DESCRIPTION OF THE DRAWINGS

Non-limiting and non-exhaustive embodiments are described with reference to the following figures, which are not necessarily drawn to scale, wherein like reference numerals refer to like parts throughout the various views unless otherwise specified.

DETAILED DESCRIPTION

Figure 1:
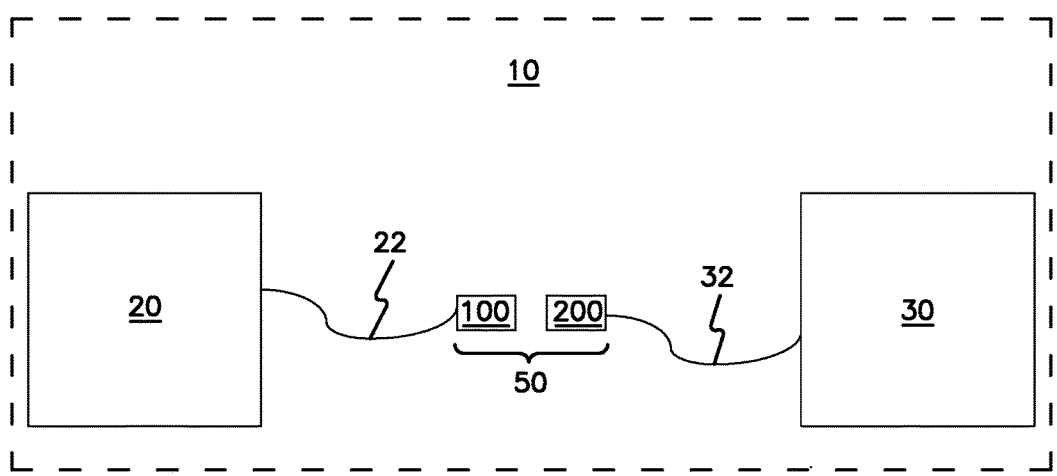
FIG. 1 is a schematic view of an example system including first and second pieces of processing equipment and an aseptic coupling device forming a sterile connection therebetween.

Various embodiments will be described in detail with reference to the drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the appended claims.

As used herein, the term "sterilize" means a process of freeing, to a specified degree, a surface or volume from microorganisms. In example embodiments, the sterility of various components can be achieved using one or more sterilization techniques, including gamma irradiation, E-beam, ethylene oxide (EtO), and/or autoclave technologies.

As used herein, the term "aseptic" refers to any process that maintains a sterilized surface or volume.

As used herein, the term "fluid" means any substance that can be made to flow including, but is not limited to, liquids, gases, granular or powdered solids, mixtures or emulsions of two or more fluids, suspensions of solids within liquids or gases, etc.

Referring now to FIG. 1, an example system 10 is shown. System 10 includes a first piece of processing equipment 20 and a second piece of processing equipment 30. In example embodiments, equipment 20 and 30 are bioreactors including biomaterial. In other embodiments, equipment 20 and 30 can be other apparatuses that require a sterile connection therebetween such as, for example, a bioreactor and a media bag or other receptacle.

Equipment 20 includes a fluid pathway 22 extending therefrom that is terminated by an aseptic coupling arrangement 50 including a first aseptic coupling device 100. Likewise, equipment 30 includes a fluid pathway 32 extending therefrom that is terminated by a second aseptic coupling device 200 of the aseptic coupling arrangement 50. In example embodiments, the environment within pathways 22 and 32 and aseptic coupling devices 100 and 200 are sterile.

Aseptic coupling device 100 can be connected to aseptic coupling device 200. Once aseptic coupling device 100 is connected to aseptic coupling device 200, a sterile fluid pathway is established between equipment 20 and equipment 30. Once the sterile fluid pathway is established, fluid can be transferred from equipment 20 to equipment 30, or vice versa.

Figure 2:
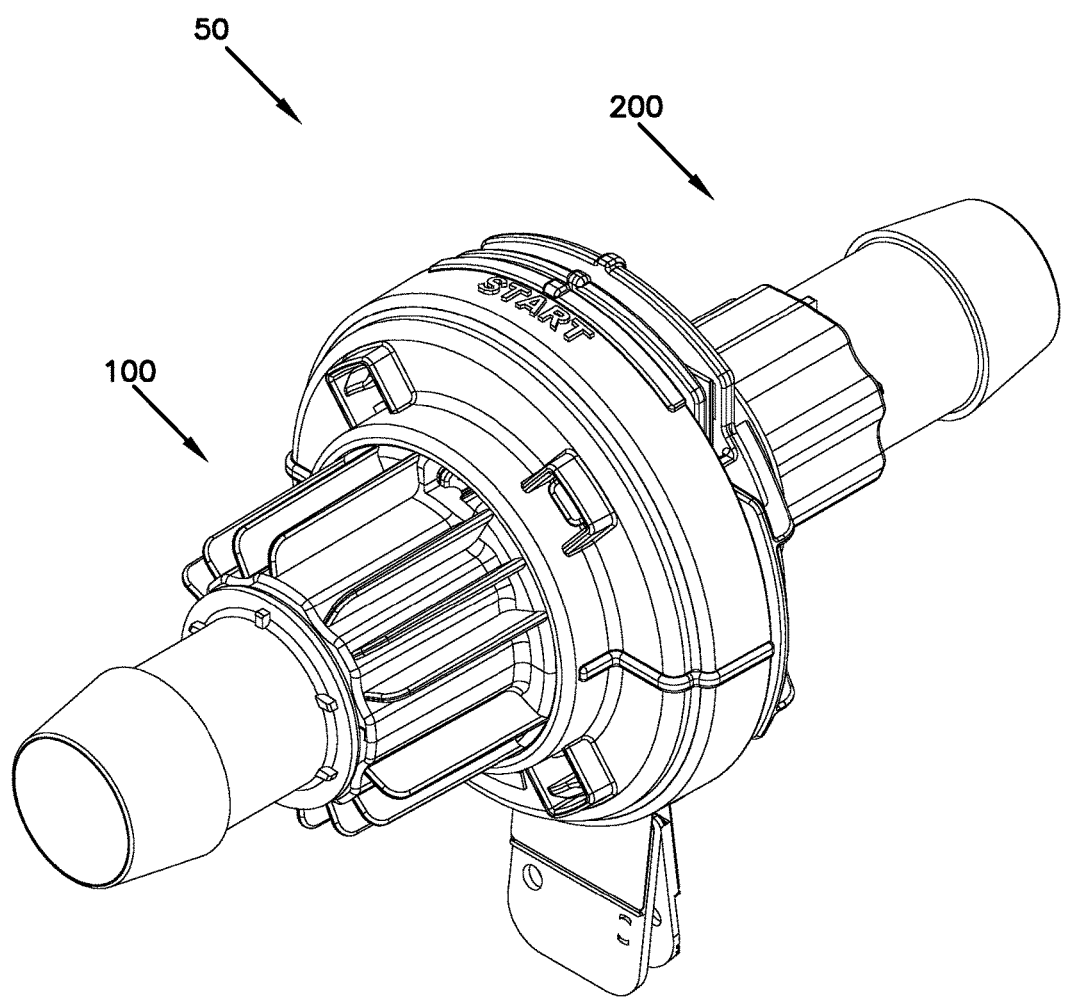
FIG. 2 is a perspective view of an example aseptic coupling arrangement in a pre-coupled state.
Figure 3:
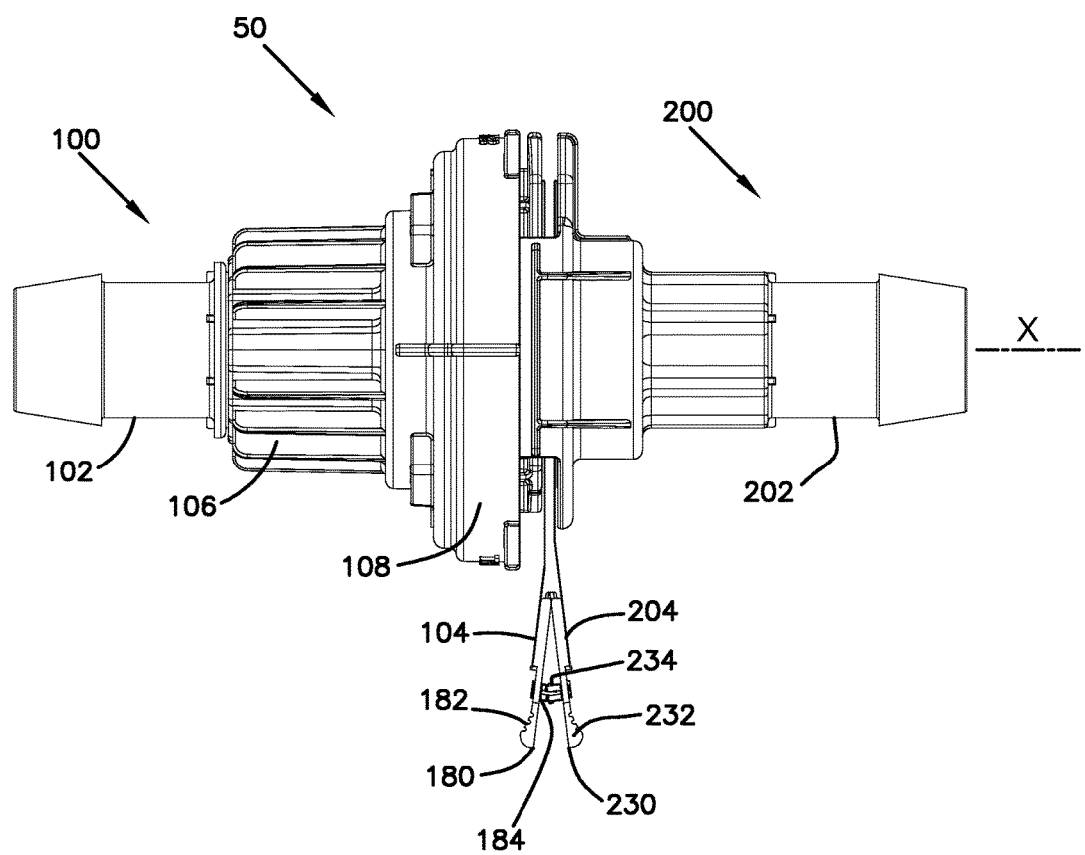
FIG. 3 is a side view of the aseptic coupling arrangement of FIG. 2.
Figure 4:
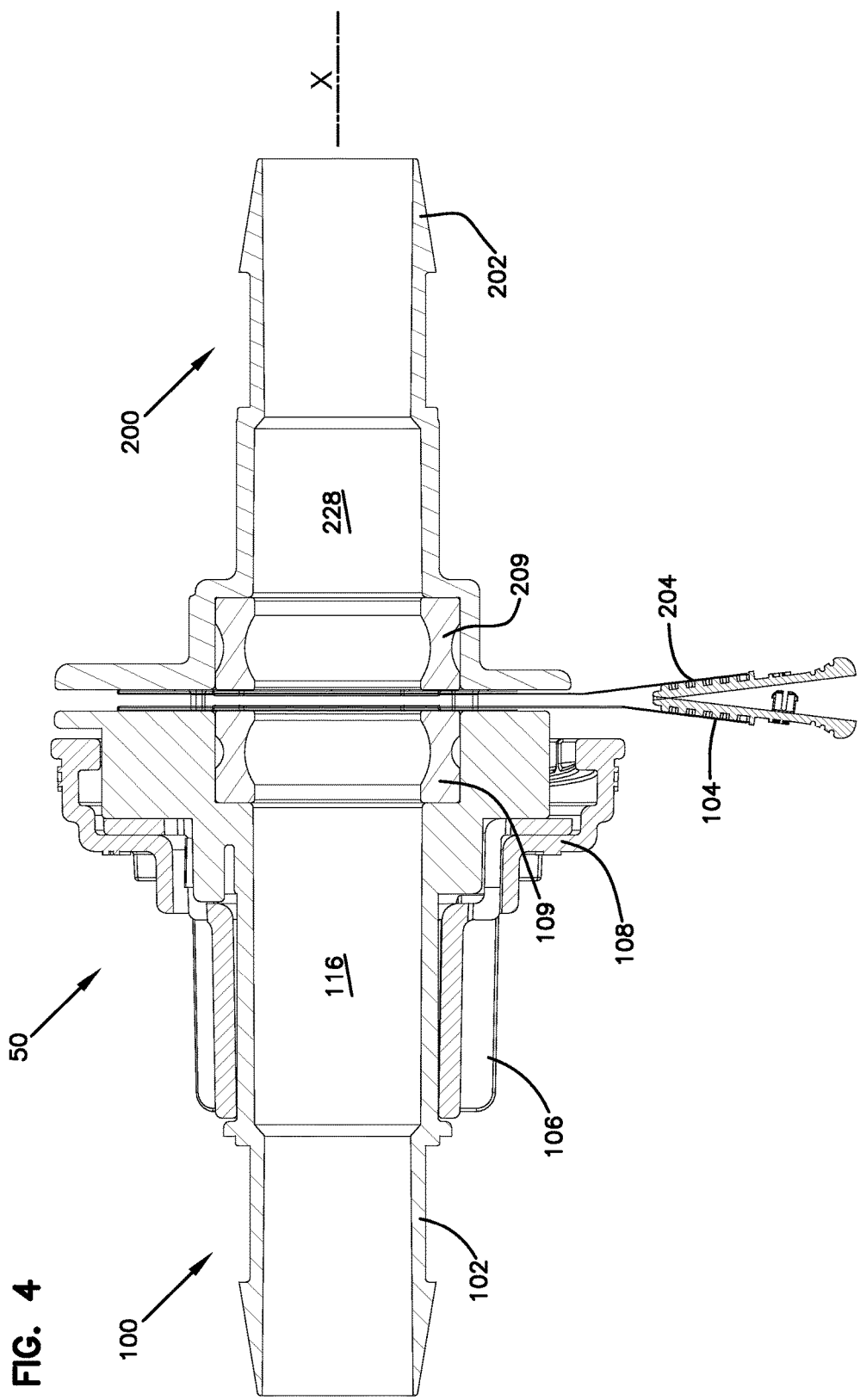
FIG. 4 is a cross-sectional view of the aseptic coupling arrangement of FIG. 3.

Referring now to FIGS. 1-2, aseptic coupling devices 100 and 200 are shown in a pre-coupled state. In this state, the aseptic coupling device 100 is received into a portion of aseptic coupling device 200. However, a sterile flow path has not yet been created because membranes associated with the aseptic coupling devices 100, 200 have not yet been removed.

In the example shown, aseptic coupling device 100 is a male coupling device, and aseptic coupling device 200 is a female coupling device. For ease of reference, device 100 may be referred to as male coupling device 100 and device 200 may be referred to as female coupling device 200. However, it should be understood that the concepts presented herein are not limited to only those embodiments where coupling device 100 is a male coupling device and where coupling device 200 is a female coupling device. In the example shown, the devices 100, 200 are keyed so that the devices 100, 200 can only be coupled in one manner, as described below. In alternative embodiments, other configurations are possible.

In the example shown, the male aseptic coupling device 100 includes a main body 102, a membrane 104, a ring adapter 106, a locking ring 108, a sealing member 109, and a removable cover 300.

As most easily viewed at FIGS. 7-10, the main body 102 has a first open end 112 and a second open end 114 through which a fluid passage 116 is defined. As most easily seen at FIG. 10, the main body 102 defines a first, second, and third internal diameter $D_1$, $D_2$, and $D_3$ along fluid passage 116. The third diameter $D_3$ is provided at a dimension that is sufficient to allow for insertion into a conduit (i.e. pathway 22), such as a hose or tube, having a nominal internal diameter. The second diameter $D_2$ is provided at a dimension that is generally about the same as the nominal internal diameter of the conduit to which the main body 102 is designed for connection. When $D_3$ is provided at a sufficient dimension, $D_2$ can be designed to provide a 1 inch flow. In one embodiment, the third diameter $D_3$ is provided at a dimension that is generally about the same as or slightly less than the external diameter of sealing member 109. At a location where the first and second internal diameters $D_1$, $D_2$ adjoin, a seal seat 138 is formed for supporting and forming a seal with sealing member 109.

Figure 19:
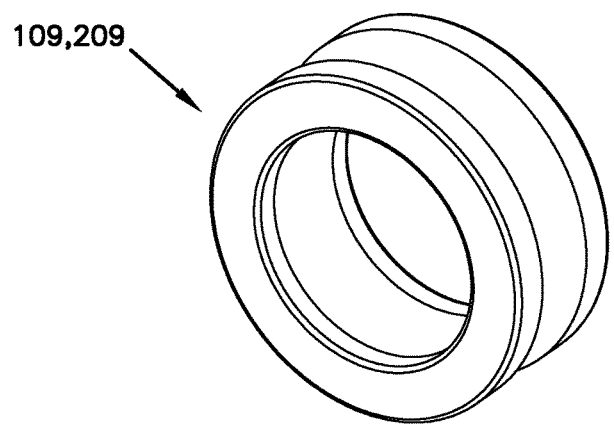
FIG. 19 is a perspective view of a sealing member used on the male and female aseptic couplings of FIG. 2.
Figure 20:
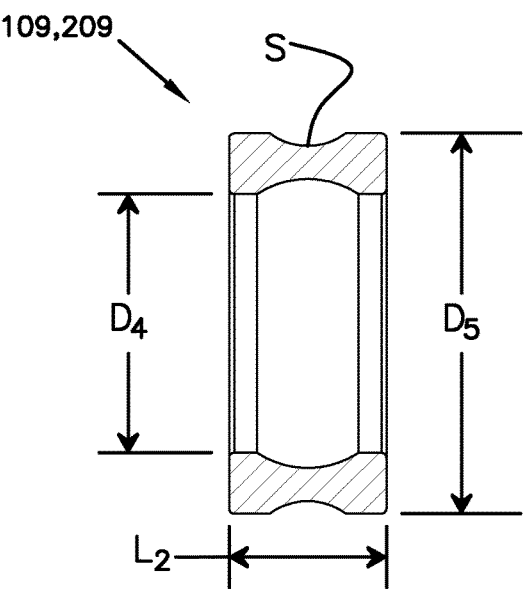
FIG. 20 is a side view of the sealing member of FIG. 19.
Figure 21:
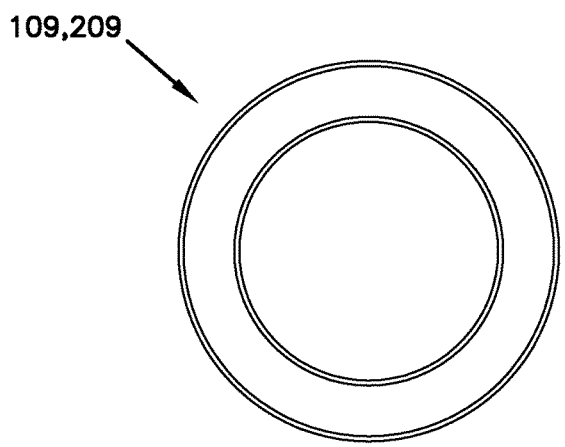
FIG. 21 is an end view of the sealing member of FIG. 19.

Sealing member 109 is shown in further detail at FIGS. 19-21. In the embodiment shown, the seal seat 138 is located a distance $L_1$ from a first face 118 of the main body 102. Sealing member 109 has a thickness $L_2$ that is slightly greater than $L_1$ to ensure that the sealing member 109 makes sufficient contact with the corresponding sealing member 209 in the main body 202 and seal seat 138 to form an aseptic seal. Sealing member 109 also has an internal diameter $D_4$ that is about the same dimension as second diameter $D_2$. Sealing member 109 also has an external diameter $D_5$ that is about the same dimension as first diameter $D_1$. Sealing member 109 also has a sidewall S that has a reduced thickness at the midpoint of the sidewall S. This structure enhances the axial compression performance of the sealing member 109 while ensuring that flow through the sealing member 109 is not restricted by the unintended formation of an inwardly extending bulge under compression. This structure also provides for enhanced sealing when the system is pressurized.

In the exemplary embodiment shown, diameter $D_1$ is about 1.5 inch, for example 1.49 inch; diameter $D_2$ is about 1 inch, for example 1.04 inch; diameter $D_3$ is about 1 inch, for example 0.92 inch; diameter $D_4$ is about 1 inch, for example 1.02 inch; diameter $D_5$ is about 1.5 inch, for example 1.50 inch; length $L_1$ is about 0.6 inch, for example 0.59 inch; length $L_2$ is about 0.6 inch, for example 0.62 inch; and the nominal internal diameter of the pathway 22 is about 1 inch, for example 1.0 inch. These dimensions are generally applicable for a 1 inch nominal termination. One skilled in the art will appreciate that other dimensions are possible, for example where the nominal termination is ¾ inch or 1½ inch.

The first end 112 of the main body 102 is the end which interfaces with the female coupling device 200. As shown, the first end 112 includes a first face 118 and a second face 120 that are spaced from each other by a plurality of ribs 122. The first face 118 and ribs 122 provide structure for ensuring aligned engagement with the female coupling device 200.

The first face 118 and ribs 122 also include features to prevent the main body 102 of the male coupling device 100 from rotating with respect to the main body 202 of the female coupling device 200 once the main body 102 is received into the female coupling device 200. In part, this is accomplished by a first alignment feature 124 that is configured to align with a corresponding alignment feature 214 on the main body 202. When main bodies 102, 202 are aligned together by the alignment features 124, 214, the alignment feature 124 is disposed between first and second securing arms 210, discussed later, on the main body 202 which prevent the main bodies 102, 202 from rotating with respect to each other.

A further visual indication of alignment is provided by the alignment of protrusions 124a and 214a on alignment features 124 and 214, respectively. Tabs 126 are also provided on the first face 118 that engage an end opposite alignment feature 124 on the securing arms 210 that further prevent the main bodies 102, 202 from being able to rotate with respect to each other.

In the exemplary embodiment shown, a rib 122 is also provided at each tab 126 to provide further engaging structure. Although two securing arms 210 and three alignment features (feature 124 and tabs 126) are shown, one skilled in the art, upon learning of the disclosed concepts presented herein, will appreciate that other numbers and configurations of alignment features and securing arms may be utilized to achieve the same positioning and anti-rotation functions.

The first face 118 of main body 102 and the securing arms 210 are also complementarily shaped to ensure that the first face 118 of main body 102 and a first face 208 of the main body 202 can be engaged together only in a single orientation and only by movement along the longitudinal axis X of the bodies 102, 202. This arrangement prevents a user from sliding the faces 118 and 208 against each other and potentially damaging the aseptic seal provided by the membranes 104, 204, discussed later, attached to each coupling device 100, 200.

This arrangement also ensures that the bodies 102, 202 are aligned in the proper orientation with the membranes of each coupling 100, 200 extending in the same direction. Although securing arms 210 and first face 118 are shown as having complementing curved shapes, one skilled in the art, upon learning of the disclosed concepts presented herein, will appreciate that other complementary shapes may be utilized to ensure the same aligned engagement function.

The first face 118 of the main body 102 further includes a pair of stand-off protrusions 128 configured to engage a corresponding pair of stand-off protrusions 216 on the first face 208 of main body 202 of the female coupling device 200. The stand-off protrusions 128, 216 ensure that the first faces 118, 208 have a clearance between them and do not fully compress against each other when the coupling devices 100, 200 are placed in a coupled state. As configured, stand-off protrusions 128, 216 help to stabilize the connection to reduce the possibility of side load induced leakage. One skilled in the art, upon learning of the disclosed concepts presented herein, will appreciate that more or fewer stand-off protrusions may be provided to ensure the same stated functionality.

The first face 118 also includes surface locations 130a, 130b to allow for membrane 104 to be attached to the front face. In one embodiment, the surface locations 130a, 130b are provided with an adhesive to which the membrane is adhered. In one embodiment, the adhesive can be provided on the membrane 104 which can be subsequently attached to surface locations 130a, 130b. In one embodiment, the membrane 104 is heat welded to the first face 118. In such an embodiment, surface locations 130a, 130b are not necessarily required.

As shown, the second end 114 of the main body 102 is configured to be connected to a fluid pathway via a connection feature 132. In the example shown, the connection feature 132 is barbed to form a hose barb (HB) type connection so that the main body 102 can be connected to a fluid pathway (e.g., 22) such as a tube or hose of a specified diameter, for example ¾", 1", and 1½". Instead of a barbed connection feature, a sanitary type connection feature may be provided.

The main body 102 also includes a ridge member 134. Ridge member 134 and the second face 120 of the main body 102 are configured to retain the ring adapter 106, discussed later, such that the ring adapter 106 can rotate about the main body 102.

The main body also includes a plurality of tabs 136 for guiding and indexing the rotation of the ring adapter 106. In the embodiment shown, one of the tabs 136a has a length, extending in a direction parallel to the longitudinal axis X, sufficient to engage with a first indexing feature 150 and a second indexing feature 152 provided on the ring adapter 106. Tab 136a functions as a surface against which the indexing features 150 and 152 can snap against to provide rotational resistance and an audible click when the ring adapter 106 and locking ring 108 are rotated into and out of the indexed position and into the secured position, respectively.

Additionally, all of the tabs 136 have a width, in a direction extending normal from the longitudinal axis X, sufficient to hold the ring adapter 106 aligned as the ring adapter is indexed into and out of indexing positions. In the embodiment shown, four tabs 136 are provided on the main body 102 with one of the tabs 136 being an indexing tab 136a. However, more or less than four tabs 136 may be provided, any or all of which may be indexing tabs 136a. Additionally, tabs 136 also act as stop members to prevent reverse rotation of the ring adapter 106 from the secured position back towards the initial indexed position by engagement with locking feature 154 provided on the ring adapter 106. With reference to Figures, 11-14, further details of the ring adapter 106 are shown. In the exemplary embodiment presented, ring adapter 106 is formed from two identical ring adapter halves 106a that mate together about main body 102. Mating of the adapter halves 106a is facilitated by edge projections 140, 142 provided at the edge of each half 106a. Edge projection 140 is complimentarily shaped to accept edge projection 142, thereby allowing the ring adapter halves 106a to mate together in a predetermined alignment.

Each ring adapter half 106a has at least a first exterior portion 144 and a second exterior portion 146. The first exterior portion 144 serves as a support surface for the locking ring 108, discussed later. The second exterior portion 146 is provided with a plurality of fins that form a finned structure serving as a gripping feature for a user when rotating the ring adapter 106 and the locking ring 108 to which the ring adapter 106 is connected. The fins on the second exterior portion can be sized large enough to allow for a user to have enough leverage to rotate the ring adapter 106 without requiring the application of excessive force.

Figure 14:
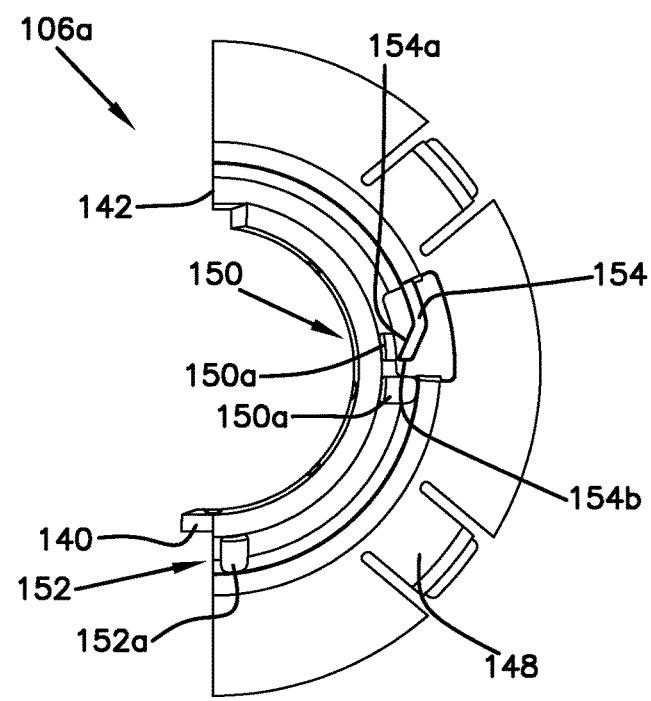
FIG. 14 is an end view of the ring adapter half of FIG. 11.
Figure 13A:
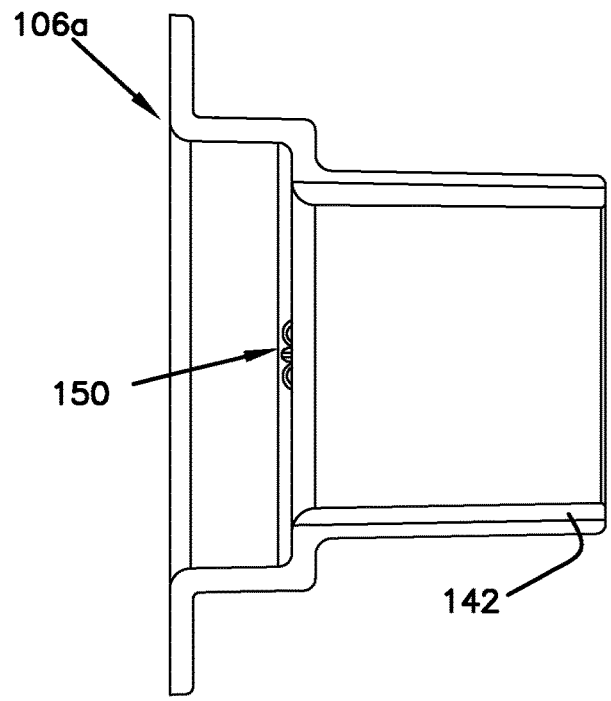
FIG. 13A is a side view of a second embodiment of a ring adapter half.
Figure 14A:
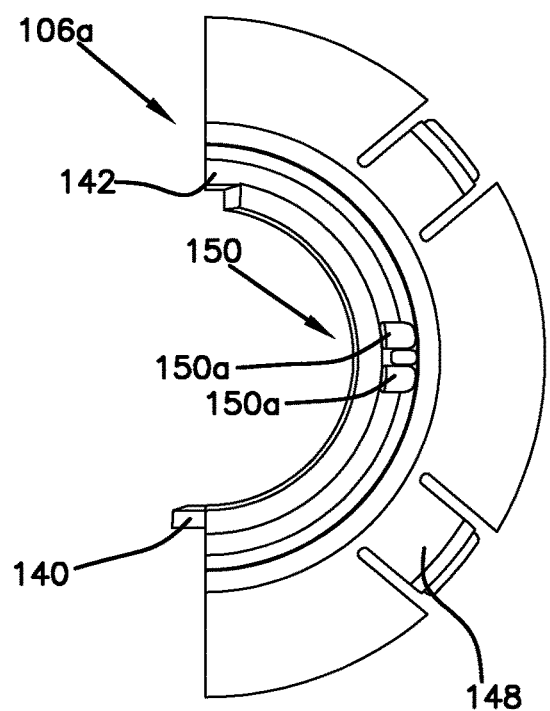
FIG. 14A is an end view of a second embodiment of a ring adapter half.
Figure 15:
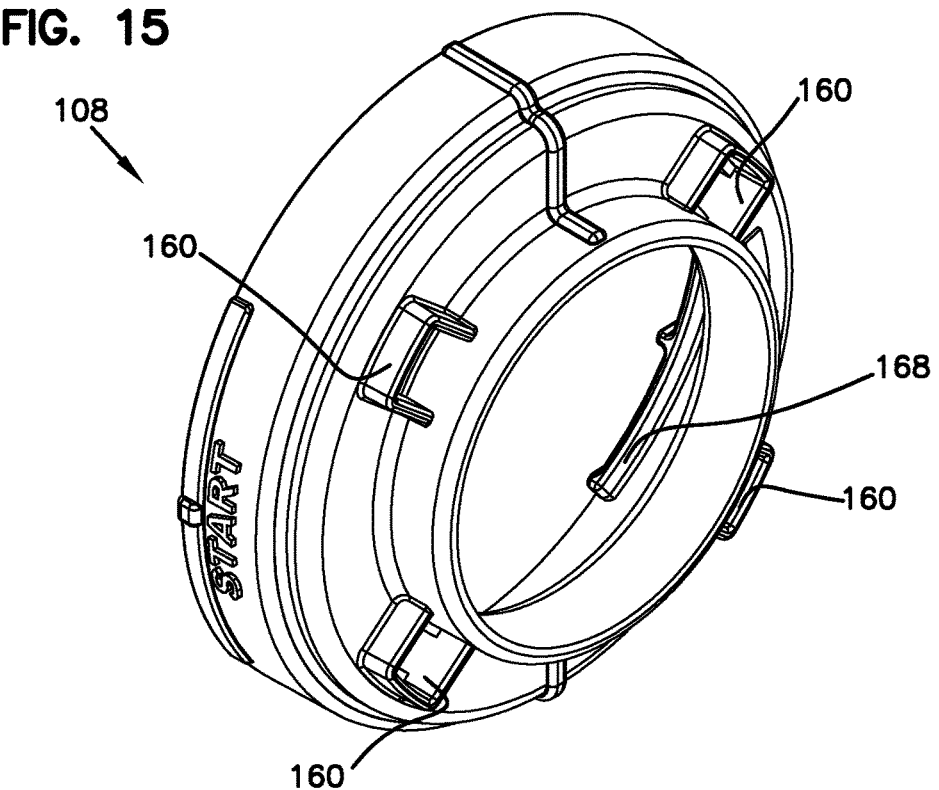
FIG. 15 is a perspective view of a locking ring of the male aseptic coupling of FIG. 2.
Figure 16:
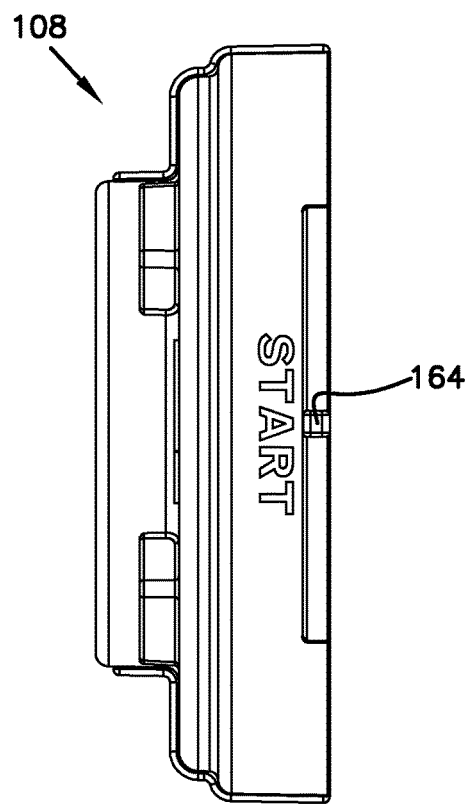
FIG. 16 is a side view of the locking ring of FIG. 15.
Figure 17:
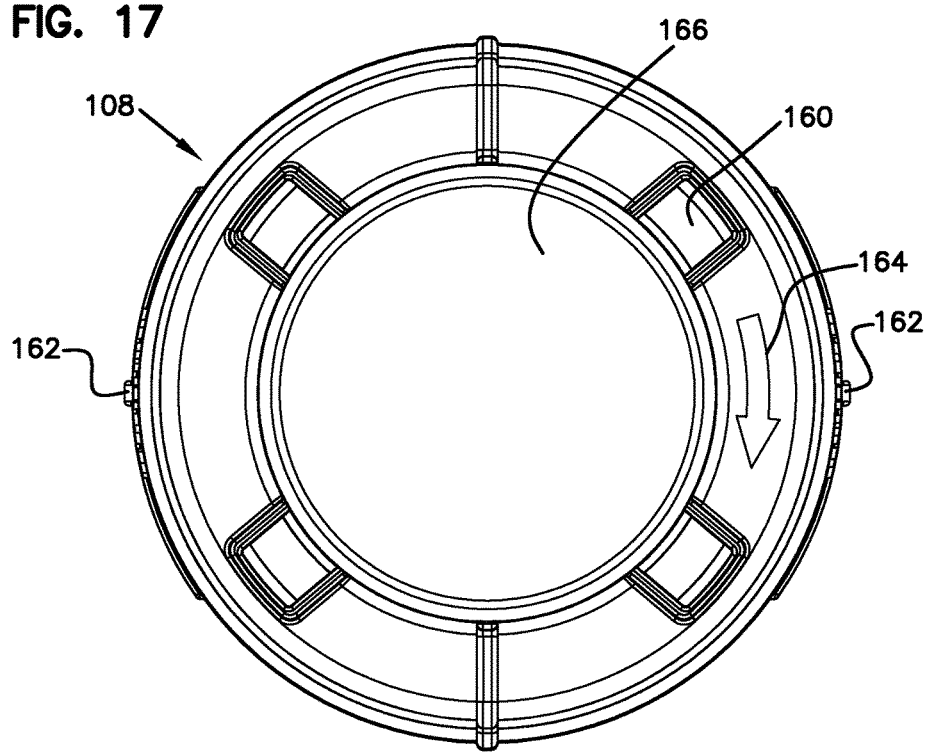
FIG. 17 is a first end view of the locking ring of FIG. 15.
Figure 18:
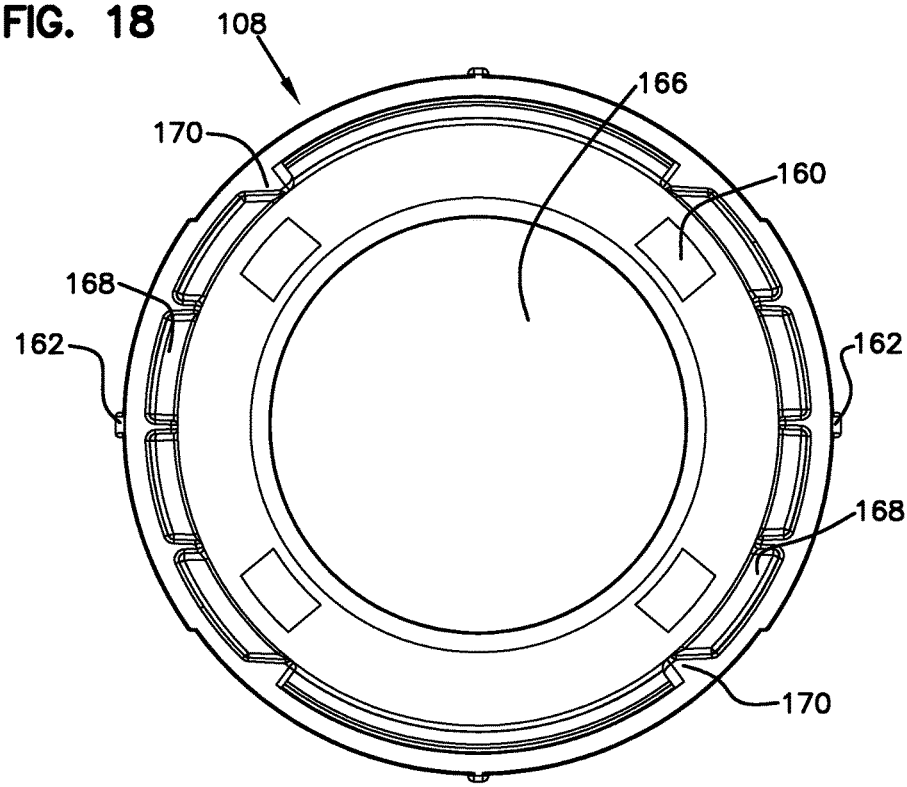
FIG. 18 is a second end view of the locking ring of FIG. 15.
Figure 16A:
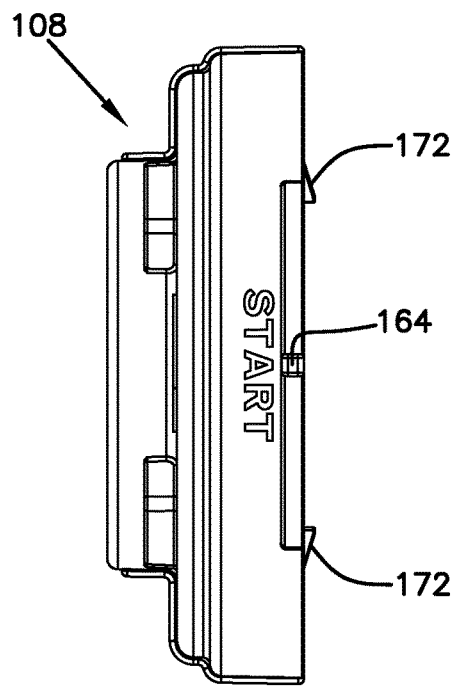
FIG. 16A is a side view of a second embodiment of a locking ring.
Figure 18A:
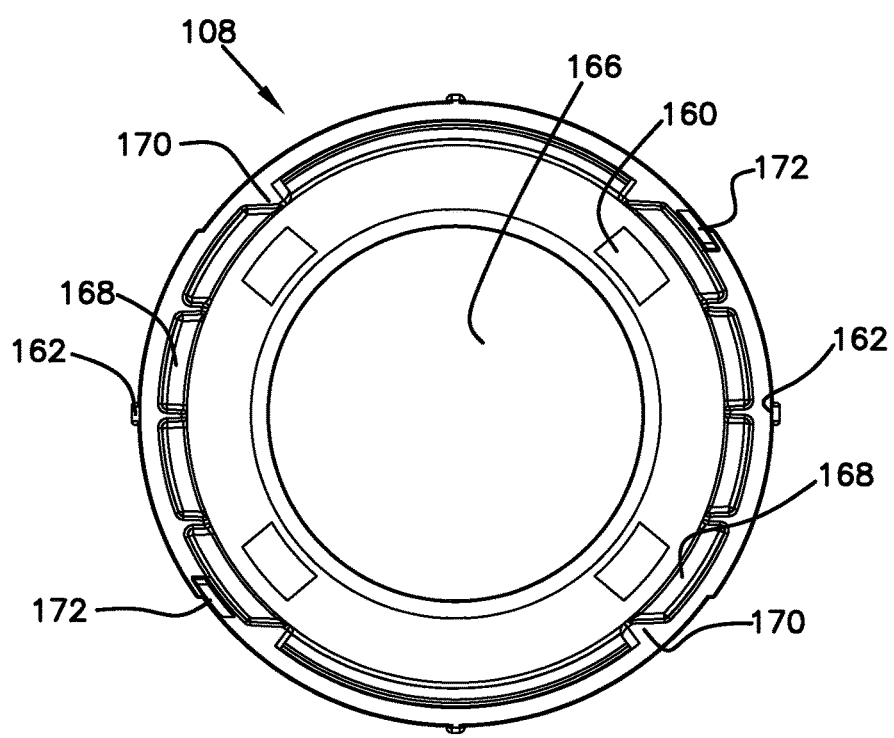
FIG. 18A is an end view of a second embodiment of a locking ring.

As described previously, the ring adapter 106 has a first indexing feature 150 that is configured to index with the indexing tab 136 on the main body 102. As most easily seen at FIG. 14, each adapter ring half 106a has a first indexing feature 150 comprising a pair of protrusions 150a. When the indexing tab 136 is between the protrusions 150a, the ring adapter 106 is in an indexed position. By applying a rotating force on the ring adapter 106, a user can cause the ring adapter to rotate into and out of the indexing position. Rotating the ring adapter 106 into or out of the indexing position can be felt by the user in the form of rotational resistance, and can also be heard as an audible clicking sound.

As each ring adapter half 106a is shown with a first indexing feature 150, the assembled ring adapter 106 has two indexing positions. As the main body 102 is shown as having a single indexing tab 136a, two indexing positions for the coupling 100 result that are separated by 180 degrees of rotation. The number and degree separation of the indexing positions can be altered by changing the number and/or location of the indexing tabs and the indexing features.

Each ring adapter half 106a is also provided with a second indexing feature 152 having a pair of protrusions 152a that operate in the same manner as protrusions 150a. In the embodiment shown, second indexing feature 152 is offset from first indexing feature 150 by about 90 degrees and corresponds to the secured position. By applying a rotating force on the ring adapter 106, a user can cause the ring adapter to rotate into the secured position. Rotating the ring adapter 106 into the secured position can be felt by the user in the form of rotational resistance, and can also be heard as an audible clicking sound.

As stated previously, a locking feature 154 is also provided on each ring adapter half 106a. The locking feature 154 engages with the tabs 136 on the main body 102 to prevent the ring adapter 106 from rotating in a reverse direction once rotated into the secured position. This is accomplished by providing a ramped surface 154a and a locking surface 154b. As the ring adapter 106 is rotated out of the indexed position and towards the secured position, the ramped surface 154a engages tab 136. As rotation continues, the locking feature 154 is deflected outwards and the ramped surface 154a therefore causes rotational resistance. As rotation further continues, the ramped surface 154a moves past tab 136 and is no longer engaged with tab 136. Once rotation has occurred to this point, the locking surface 154b will engage with the tab if reverse rotation is attempted, thereby locking the ring adapter 106 in the secured position. As a locking feature 154b is provided on each ring adapter half 106a, the above described operation occurs at two locations simultaneously. It is noted that fewer or more locking features 154 may be provided on ring adapter 106. In the embodiment shown with four tabs 136 and two locking features 154b, it is additionally noted that the locking surfaces 154b prevent reverse rotation of the ring adapter 106 from the initially indexed position and from the secured position by engagement with tabs 136.

The ring adapter 106 is connected to the locking ring 108 via a plurality of retaining clips 148 extending through corresponding apertures 160 in the locking ring 108. In the particular embodiment shown, four retaining clips 148 and four corresponding apertures 160 are provided. In order to ensure proper alignment between the indexing feature 150 of the ring adapter 106 and the ramped surfaces 168, discussed below, of the locking ring 108, the retaining clips 148 and apertures 160 are provided in an asymmetrically spaced pattern.

The locking ring 108 is shown in further detail at FIGS. 15-18. As stated previously, locking ring 108 includes a plurality of apertures 160 for receiving the retaining clips 148 on the ring adapter 106. Locking ring defines a central aperture 166 through which the ring adapter 106 and main body 102 extend. Locking ring 108 also includes two alignment indicators 162 for ensuring that the locking ring 108 is properly aligned with the alignment protrusion 124a on the main body 102 before the main bodies 102, 202 are coupled together. The locking ring 108 also includes indicia 164 for showing the proper direction of rotation for the locking ring 108 to lock the ring onto body 202. In the embodiment shown, the indicia 164 includes the word "start." The locking ring 108 further includes stop members 170 for preventing the locking ring 108 from rotating in the reverse direction from the initial starting position. As mentioned above, locking feature 154b also performs this function. As such, embodiments including only one or both of these features are possible without departing from the concepts disclosed herein.

As stated above, the locking ring 108 includes a pair of ramp surfaces 168. Ramp surfaces 168 are for engaging corresponding ramp surfaces 218 on the main body 202 of the female coupling device 200. By rotating the locking ring 108, ramp surfaces 168 and 218 pull the main bodies 102, 202 towards each other and force a seal between sealing members 109 and 209. In the secured position, the locking ring has rotated to ensure that a sufficient compressive force exists to form a seal between the sealing members 109, 209, but not so much so that the membranes 104, 204 separating the sealing members 109, 209 cannot be removed.

Referring to FIGS. 13A, 14A, 16A, and 18A an alternative embodiment of the ring adapter half 106a and locking ring 108 are shown. In the embodiment shown, indexing feature 152 and locking feature 154 are not present on the ring adapter half and are replaced by locking features 172, located on the locking ring 108. The locking features 172 form ramped surfaces beyond which reverse rotation is prevented. In such an embodiment, the lock features 172 engage a side edge 224a of stop surface 224 attached to each securing arm 210, when rotated to the secured position. Once engaged in this position, the locking ring 108 is prevented from moving in the reverse direction by the lock features 172. One skilled in the art, upon learning of the disclosed concepts herein, will appreciate that additional ramped surfaces or other types of locking features may be used, or that ramped surfaces could be provided on only the main body 202 of the female coupling device 200 or only the locking ring 108. In other alternatives, the lock features 172 can be removed.

As stated previously, membrane 104 is coupled to the first face 118 of the aseptic coupling device 100. In examples, the membrane is coupled to the first face 118 completely around and beyond the first open end 112 of the main body 102 at attachment locations 130a, 130b. The attachment locations 130 allow membrane 104 to extend beyond the opening in the open end 112 so that as membrane 104 is removed, the sterility of open end 112 is maintained even if membranes 104, 204 are pulled at different rates.

Prior to coupling the coupling devices 100, 200 together, membranes 104, 204 are folded over their respective front faces 118, 208 such that each membrane will roll on itself and detach from the front face as it is pulled out of the aseptic coupling arrangement 50. To ensure that the membranes 104, 204 are pulled together, handles 182, 232 are provided at the ends 180, 230 of membranes 104, 204, respectively. The handles 182, 232 are connected to each other by attachment members 184, 234. Once attached, a single handle is formed that can be pulled by an operator with the assurance that the membranes 104, 204 will be removed in simultaneous or near simultaneous fashion. However, the membranes can be removed in sequential fashion as well, although sterility may be compromised.

Figure 22:
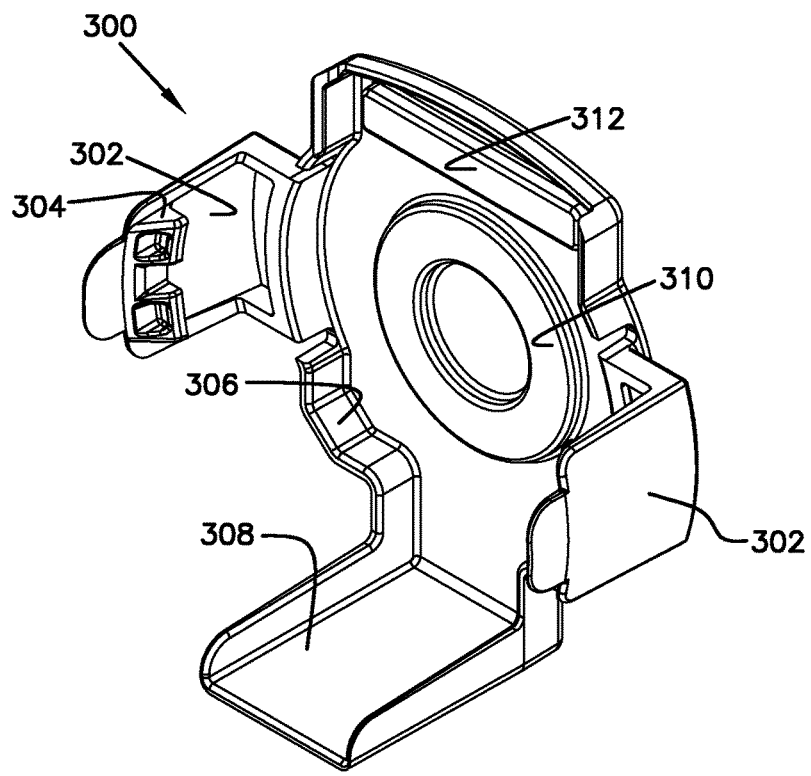
FIG. 22 is a perspective view of a cover for the male aseptic coupling of FIG. 2.
Figure 23:
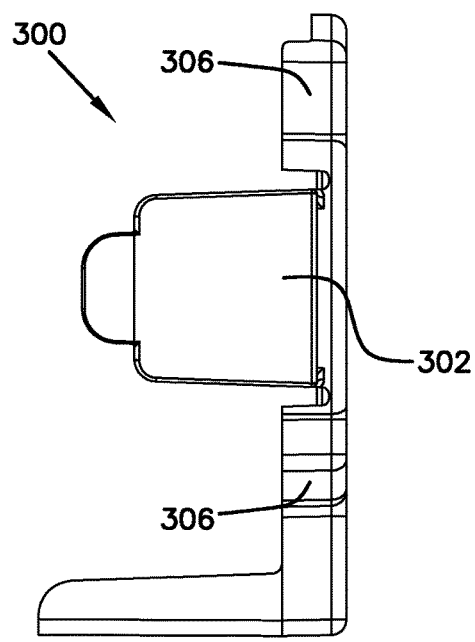
FIG. 23 is a side view of the cover of FIG. 26.
Figure 24:
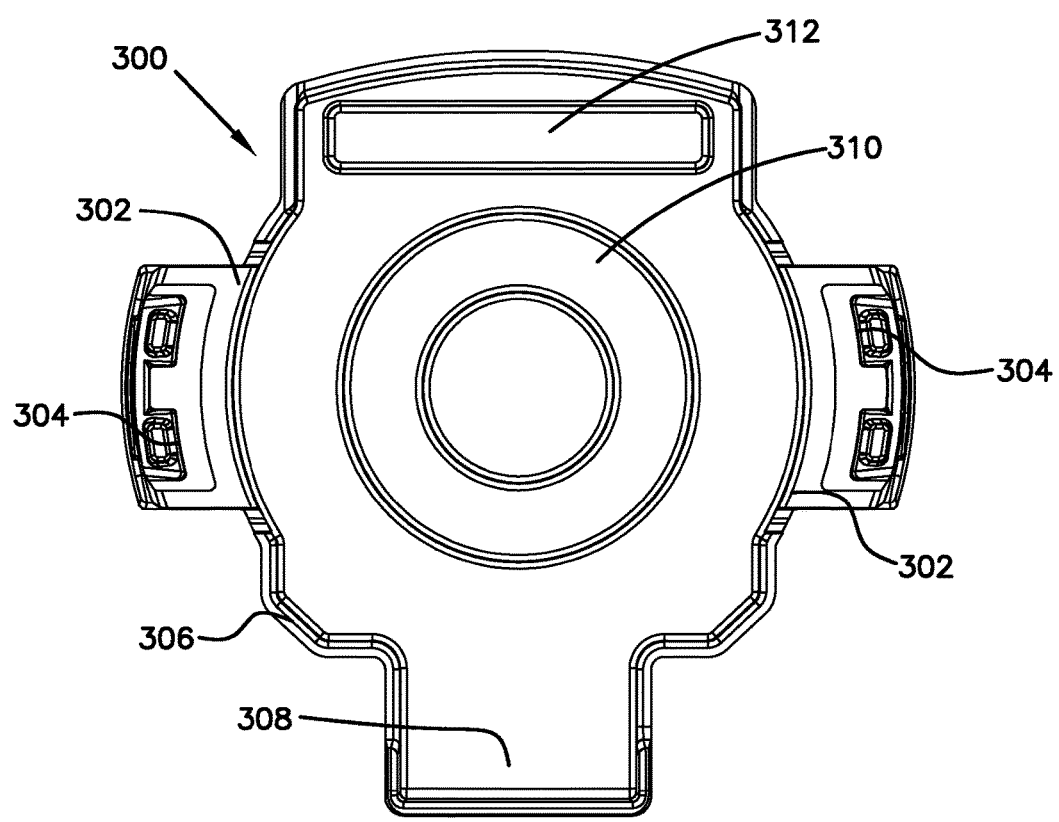
FIG. 24 is an end view of the cover of FIG. 26.
Figure 25:
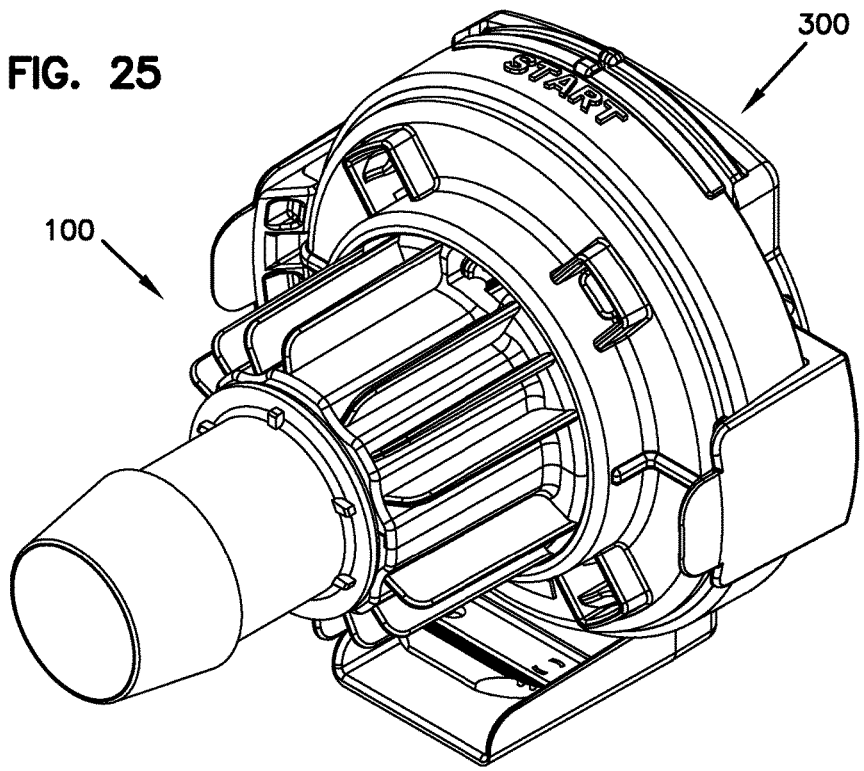
FIG. 25 is a perspective view of the cover of FIG. 22, as installed on the male aseptic coupling of FIG. 2.
Figure 26:
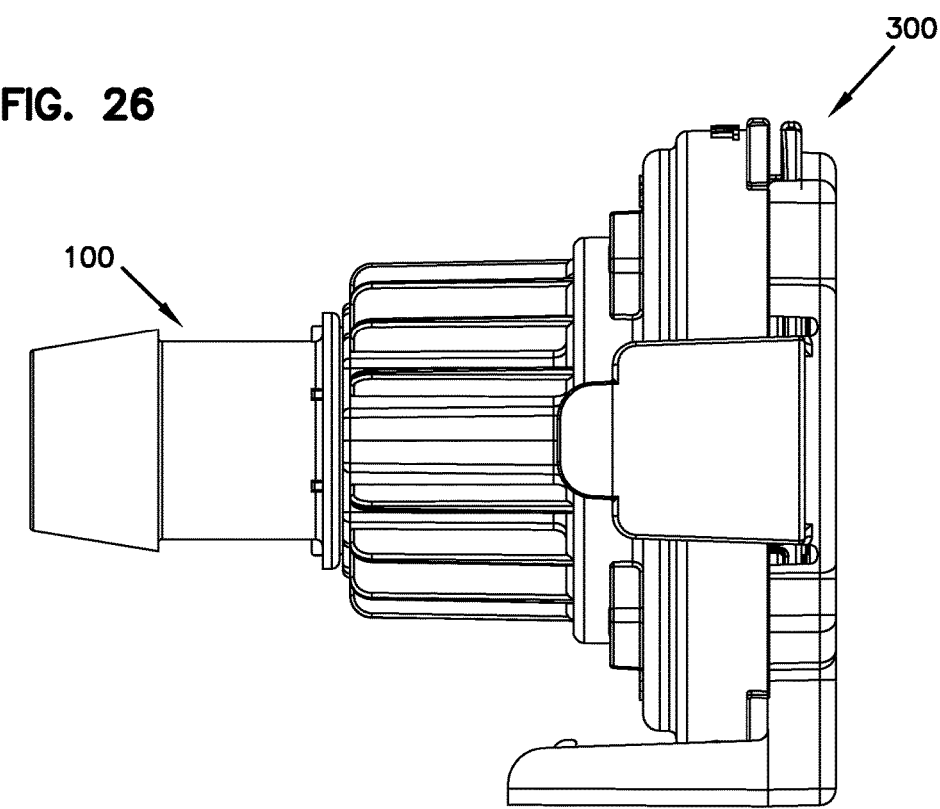
FIG. 26 is a side view of the cover of FIG. 22, as installed on the male aseptic coupling of FIG. 2.
Figure 27:
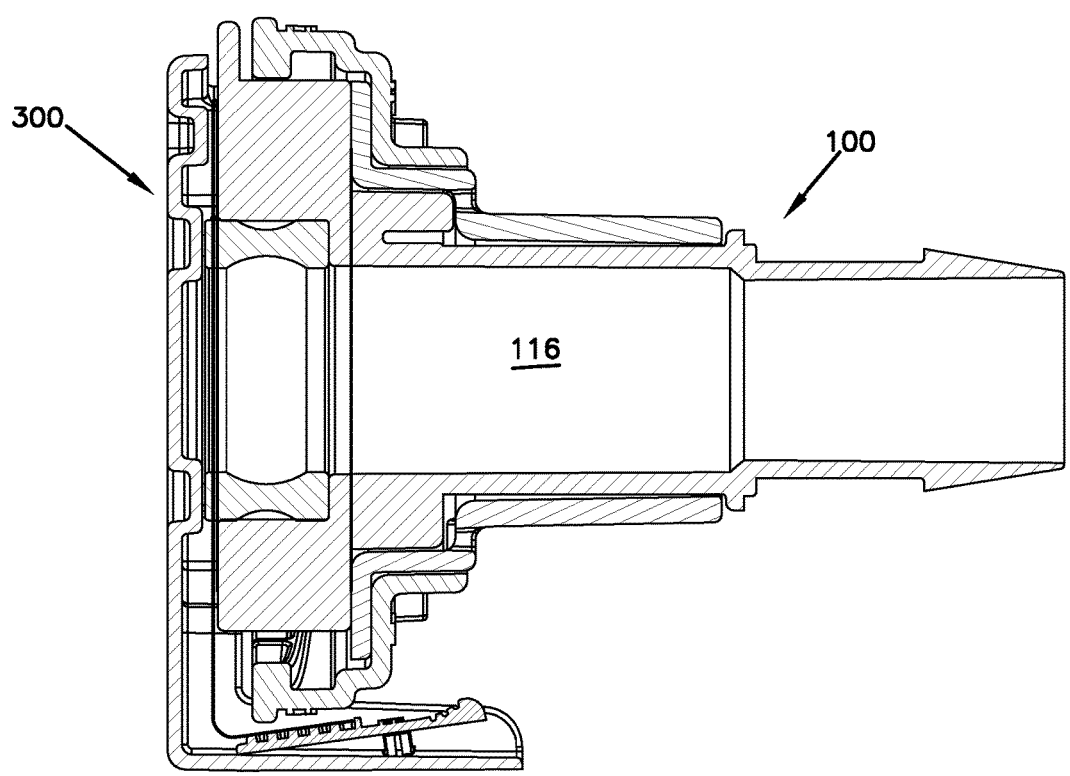
FIG. 27 is a cross-sectional side view of the cover of FIG. 22, as installed on the male aseptic coupling of FIG. 2.
Figure 28:
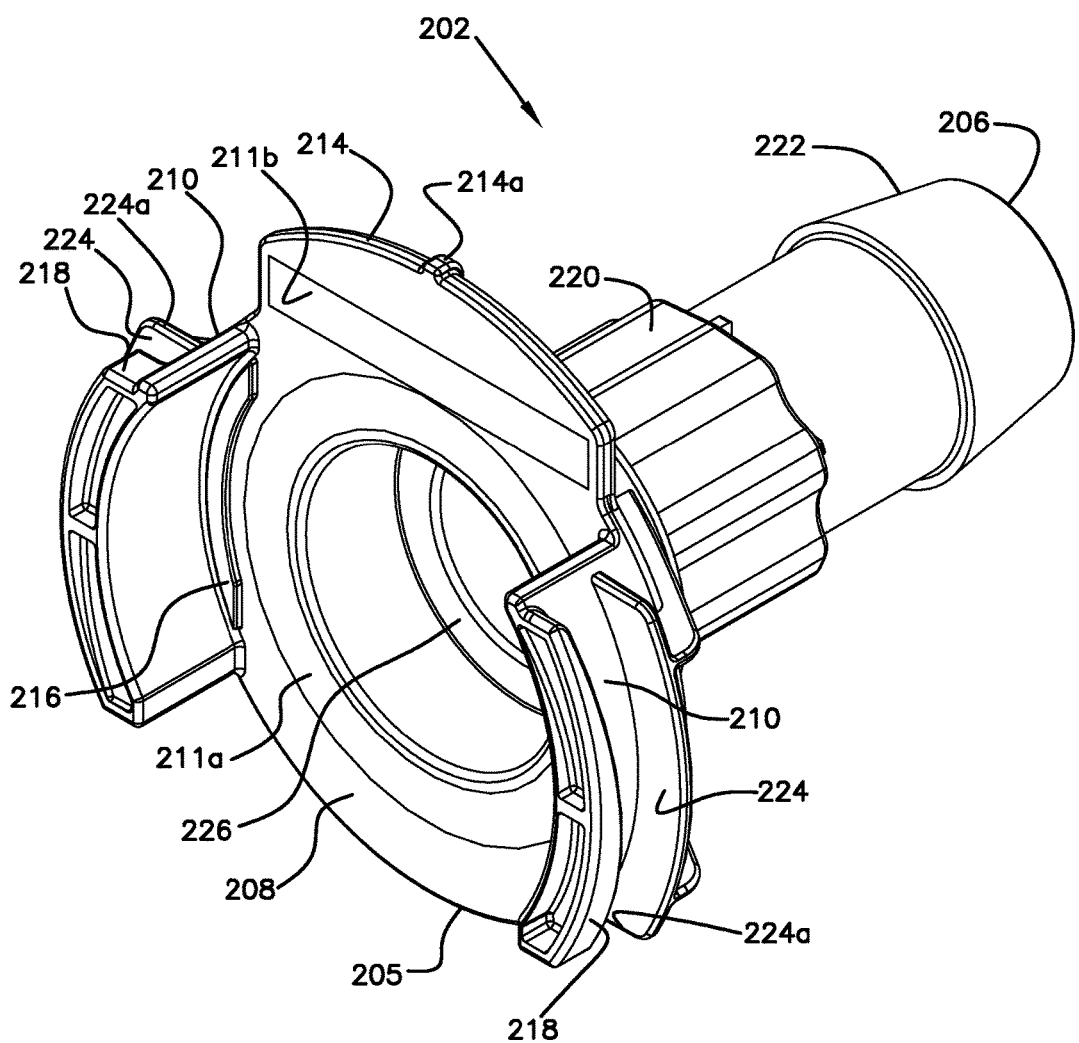
FIG. 28 is a perspective view of a main body of the female aseptic coupling of FIG. 2.
Figure 29:
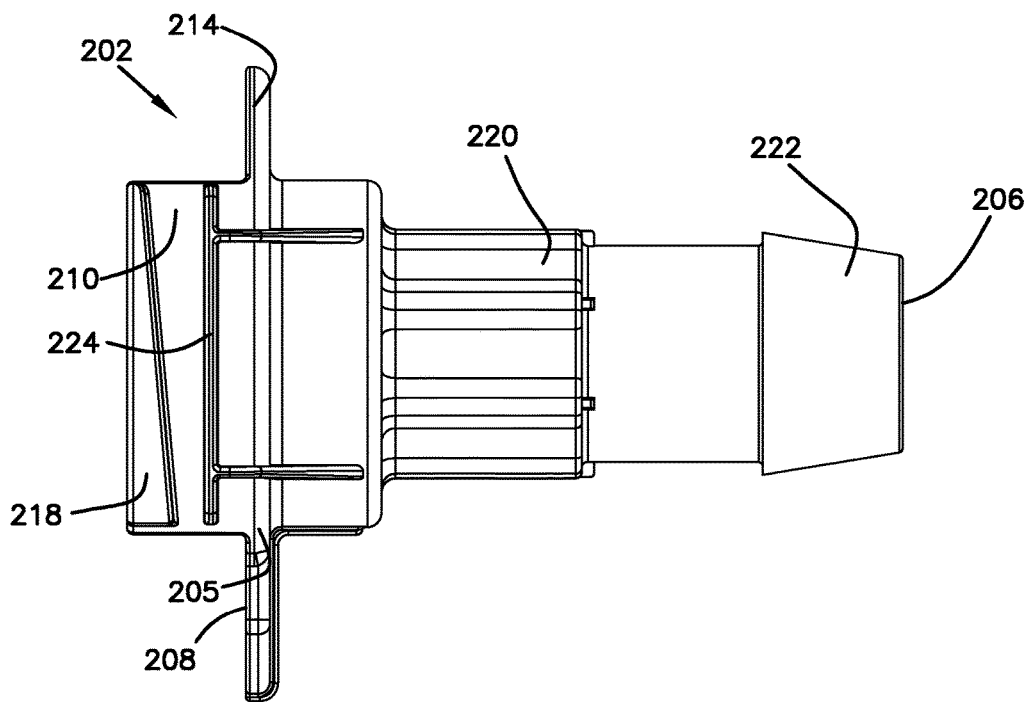
FIG. 29 is a side view of the main body of FIG. 28.
Figure 30:
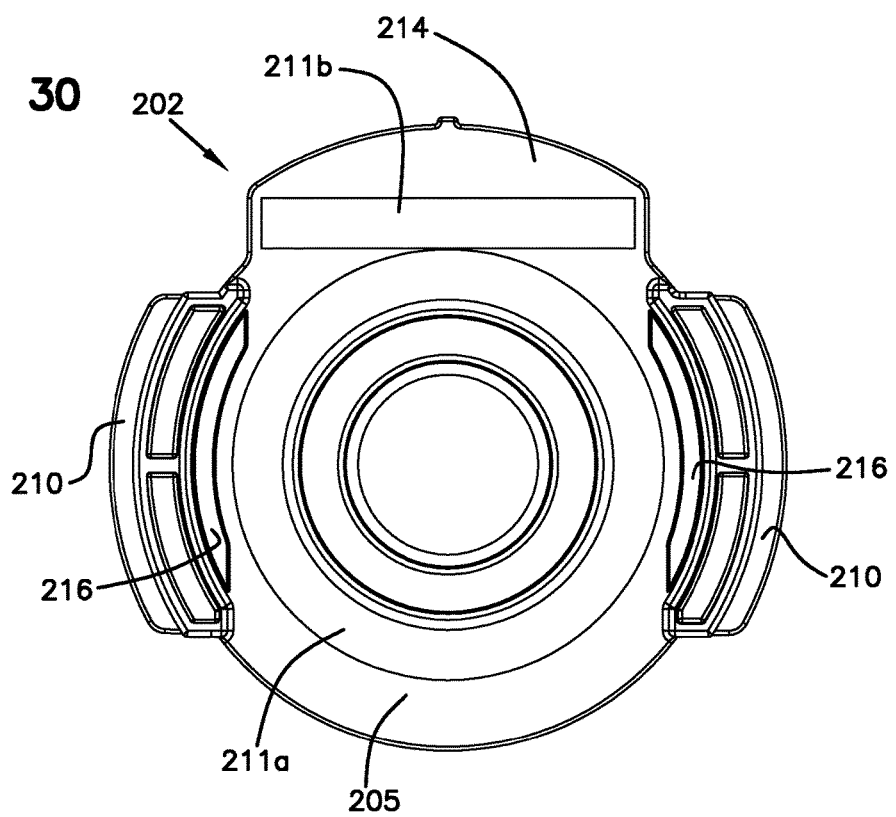
FIG. 30 is an end view of the main body of FIG. 28.

With reference to FIGS. 22-24, a cover 300 for the first aseptic coupling 100 is shown. As shown, cover 300 includes a pair of retaining arms 302 with retaining clips 304 for engaging the locking ring 108. Cover 300 further includes a sidewall 306 that surrounds a majority of the front face 118 of the main body 102. A channel 308 is also provided to hold the membrane 104 in a secure position. Cover 300 is also shown as including a raised surface 310 for aiding in retaining the sealing member 109 and the membrane 104 in a secure position. An additional raised surface 312 is provided to further retain the membrane 104 above the seal at general area of the upper attachment location 130b. FIGS. 25-27 show the cover 300 mounted onto the first aseptic coupling device 100.

Referring to FIGS. 28-31, the second aseptic coupling device 200 is shown in further detail. As mentioned previously, the aseptic coupling device 200 has a main body 202 including securing legs 210 having ramp surfaces 218 and stop surfaces 224 and including an alignment feature 214. Main body 202 also has a first open end 205 and a second open end 206 through which a fluid passage 228 is defined.

Figure 31:
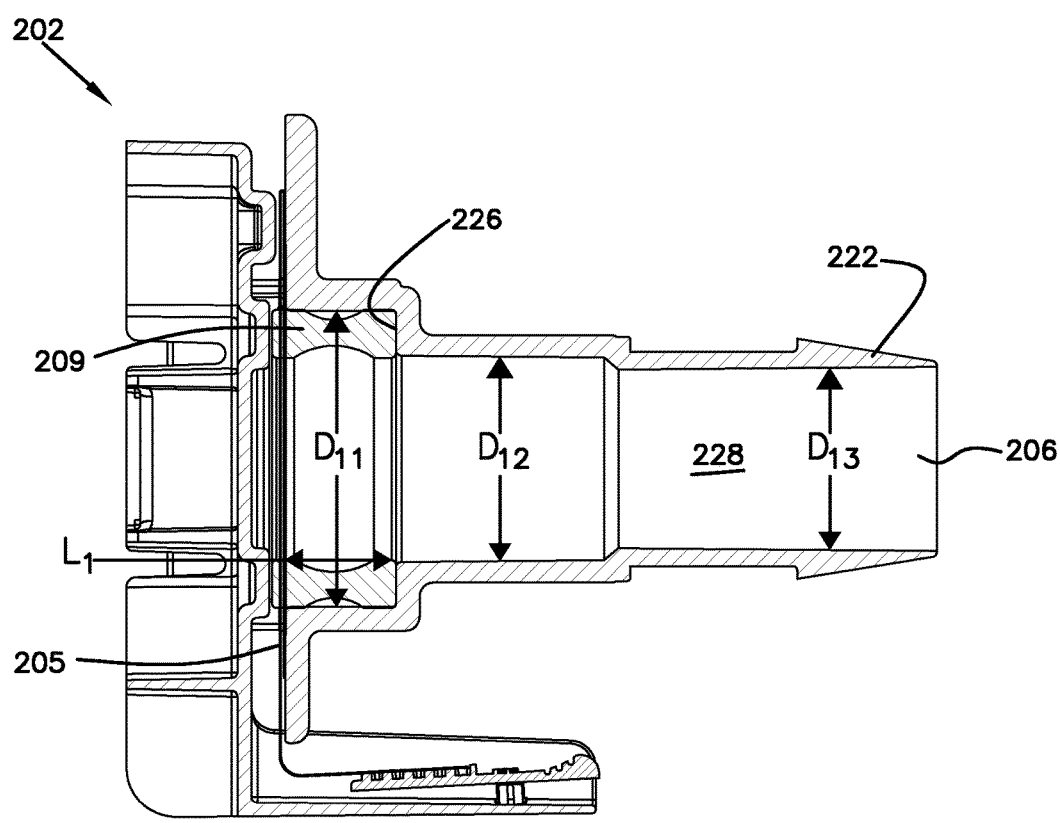
FIG. 31 is a cross-sectional side view of the main body of FIG. 28.

As most easily seen at FIG. 31, the main body 202 defines a first, second, and third internal diameter $D_{11}$, $D_{12}$, and $D_{13}$ along fluid passage 228. The diameter $D_{13}$ is provided at a dimension sufficient to allow for insertion of the second end 206 into a conduit (i.e. pathway 32), such as a hose or tube having a nominal internal diameter. The diameter $D_{12}$ is provided at a dimension that is generally about the same as the nominal internal diameter of the conduit to which the main body 202 is designed for connection. In one embodiment, $D_{12}$ is sufficiently sized to provide 1 inch flow given that $D_{13}$ is sufficiently sized. The diameter $D_{11}$ is provided at a dimension that is generally about the same as or slightly less than the external diameter of sealing member 209. At a location where the diameters $D_{11}$ and $D_{12}$ adjoin, a seal seat 226 is formed for supporting and forming a seal with sealing member 109.

Sealing member 209 is the same as that shown for sealing member 109 in FIGS. 19-21. In the embodiment shown, the seal seat 226 is located a distance $L_1$ from a first face 208 of the main body 202. Sealing member 209 has a thickness $L_2$ that is slightly greater than $L_1$ to ensure that the sealing member 209 makes sufficient contact with the corresponding sealing member 109 in the main body 102 and the seal seat 226 to form an aseptic seal. Sealing member 209 also has an internal diameter $D_4$ that is about the same dimension as second diameter $D_{12}$. Sealing member 209 also has an external diameter $D_5$ that is about the same dimension as first diameter $D_{11}$. Sealing member 209 also has a sidewall S that has a reduced thickness at the midpoint of the sidewall S. This structure enhances the axial compression performance of the sealing member 209 while ensuring that flow through the sealing member 209 is not restricted by the unintended formation of an inwardly extending bulge during compression. As stated previously, the pressurized fluid acting on the seal structure also enhances the sealing characteristics of the seal.

In the exemplary embodiment shown, diameter $D_{11}$ is about 1.5 inch, for example 1.49 inch; diameter $D_{12}$ is about 1 inch, for example 1.04 inch; diameter $D_{13}$ is about 1 inch, for example 0.92 inch; diameter $D_4$ is about 1 inch, for example 1.02 inch; diameter $D_5$ is about 1.5 inch, for example 1.50 inch; length $L_1$ is about 0.6 inch, for example 0.59 inch; length $L_2$ is about 0.6 inch, for example 0.62 inch; and the nominal internal diameter of the pathway 32 is about 1 inch, for example 1.0 inch. One skilled in the art will appreciate that other dimensions are possible.

The first face 208 of the main body also includes surface locations 211a, 211b to allow for membrane 204 to be attached to the front face 208. In one embodiment, the surface locations 211a, 211b are provided with an adhesive to which the membrane is adhered. In one embodiment, the adhesive can be provided on the membrane 204 which can be subsequently attached to surface locations 211a, 211b. In one embodiment, the membrane 204 is heat welded (or heat staked) to the front face 208. In such an embodiment, surface locations 211a, 211b are not necessarily required.

Main body 202 further comprises an exterior portion 220 that is provided with a fluted surface and serves as a gripping member for a user when rotating the ring adapter 106 and the locking ring 108 with respect to the main body 202.

As shown, the second end 206 of the main body 202 is configured to be connected to a fluid pathway via a connection feature 222. In the example shown, the connection feature 222 is barbed so that the main body 202 can be connected to a fluid pathway (e.g., 32) such as a hose of a specified diameter, for example ¾", 1", and 1½". Instead of a barbed connection feature, a sanitary type connection feature may be provided.

Figure 32:
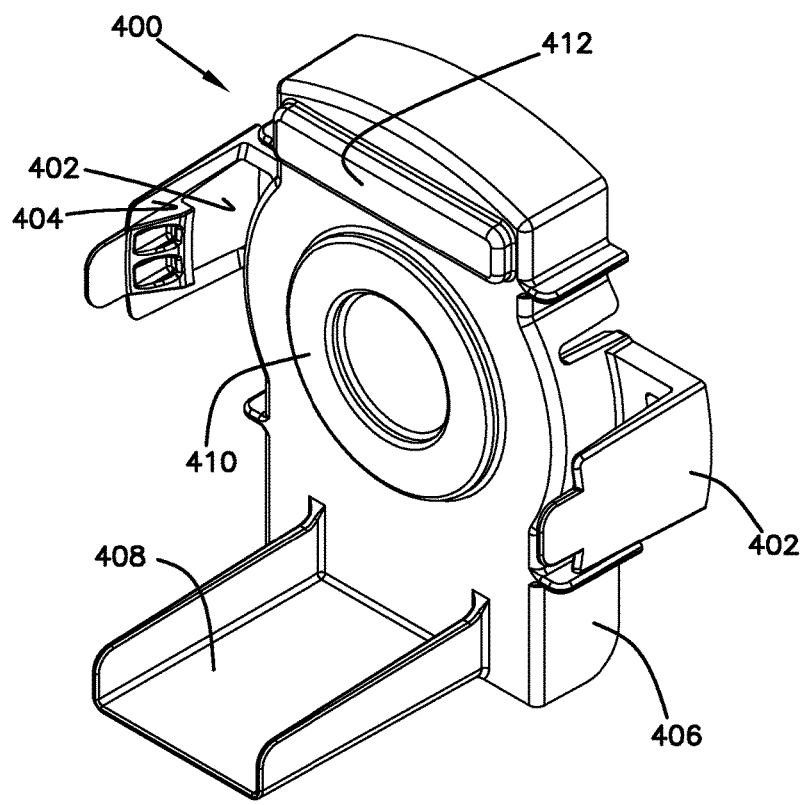
FIG. 32 is a perspective view of a cover for the female aseptic coupling of FIG. 2.
Figure 33:
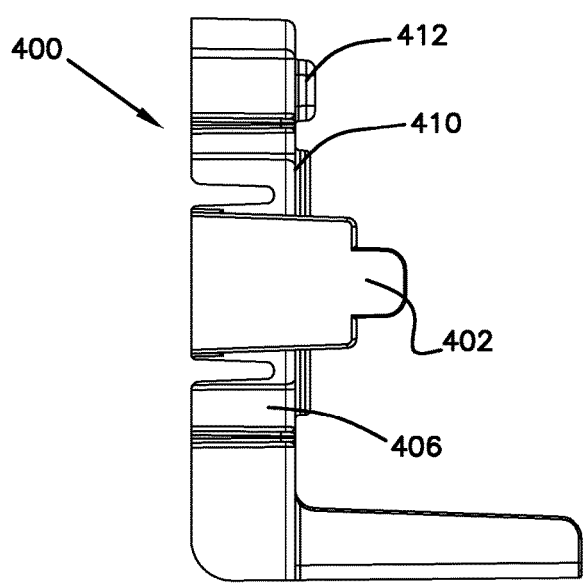
FIG. 33 is a side view of the cover of FIG. 32.
Figure 34:
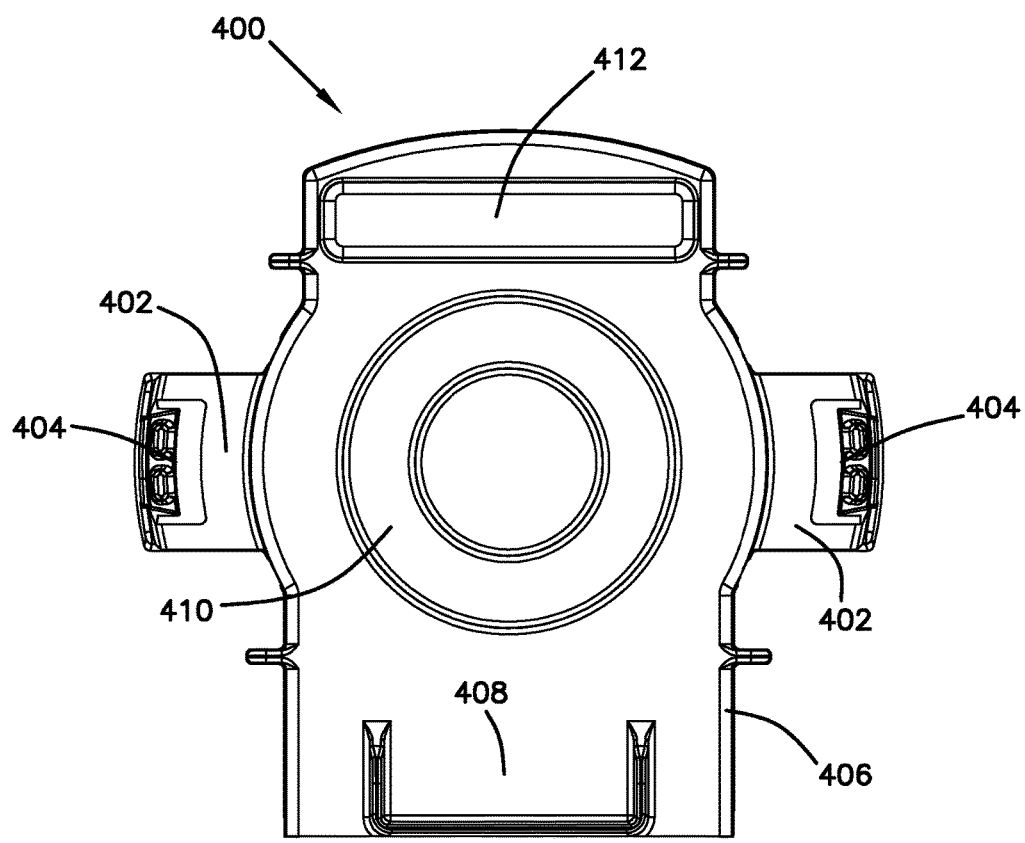
FIG. 34 is an end view of the cover of FIG. 32.
Figure 35:
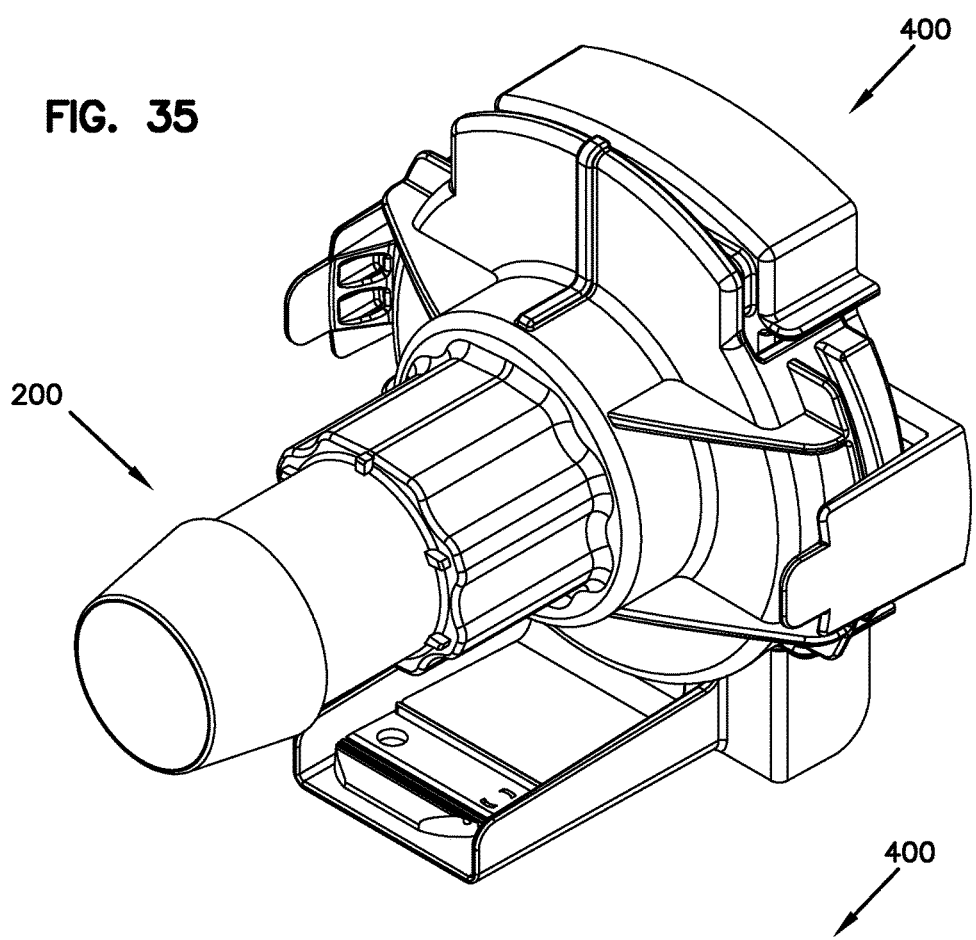
FIG. 35 is a perspective view of the cover of FIG. 32, as installed on the female aseptic coupling of FIG. 2.
Figure 36:
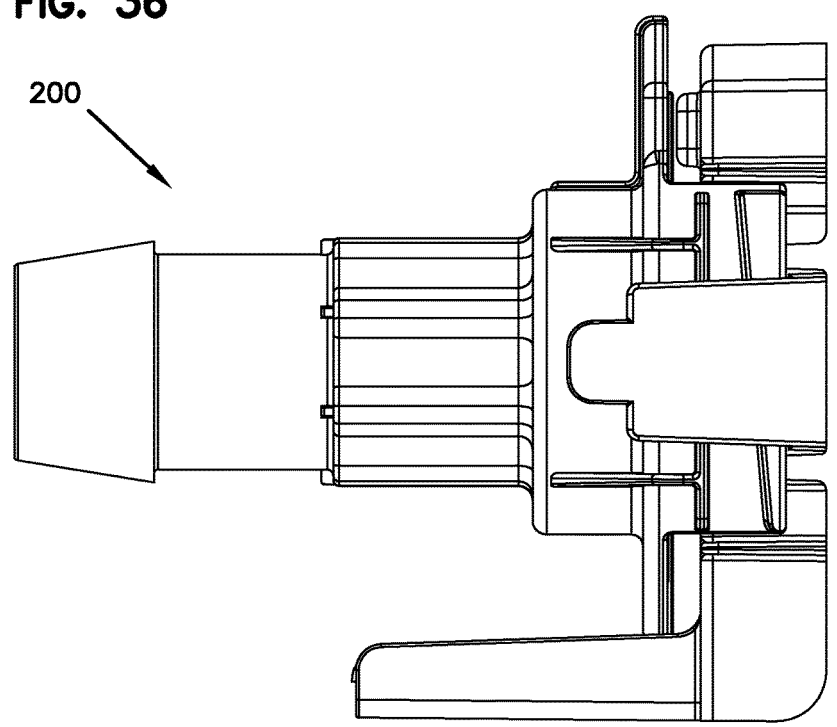
FIG. 36 is a side view of the cover of FIG. 32, as installed on the female aseptic coupling of FIG. 2.
Figure 37:
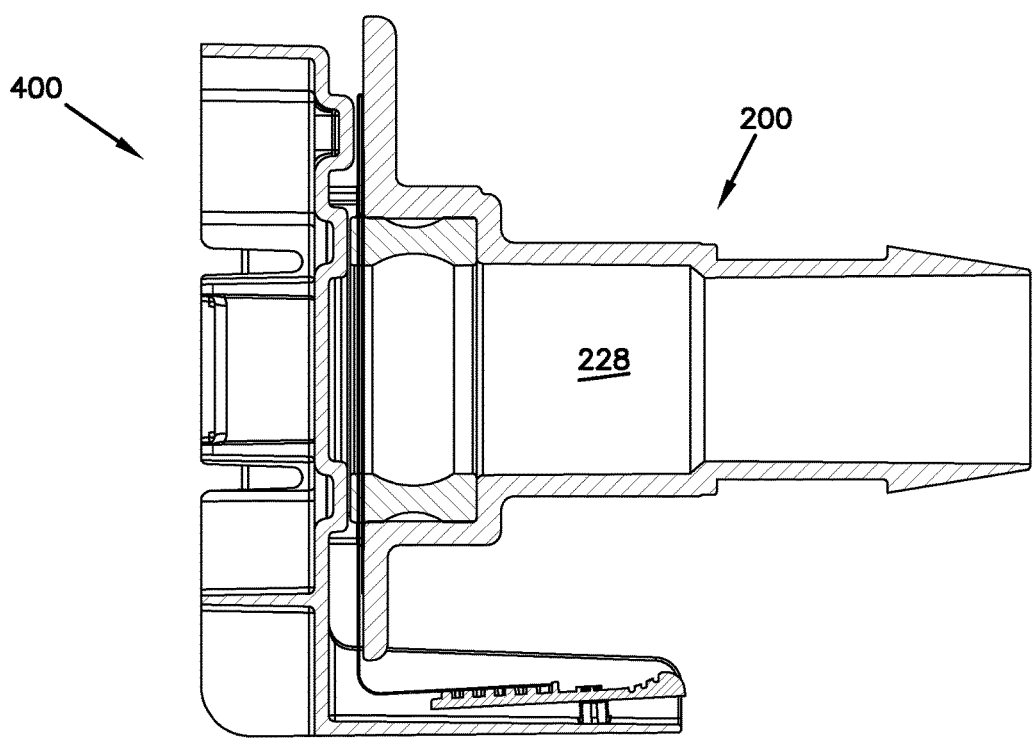
FIG. 37 is a cross-sectional side view of the cover of FIG. 32, as installed on the female aseptic coupling of FIG. 2.

With reference to FIGS. 32-34, a cover 400 for the first aseptic coupling 200 is shown. As shown, cover 400 includes a pair of retaining arms 402 with retaining clips 404 for engaging the stop surfaces 224 of the main body 202. Cover 400 further includes a sidewall 406 that engages a portion of the securing legs 210 of the main body 202. A channel 408 is also provided to hold the membrane 204 in a secure position. Cover 400 is also shown as including a raised surface 410 for aiding in retaining the sealing member 209 and the membrane 204 in a secure position. An additional raised surface 412 is provided to further retain the membrane 204 above the seal at general area of the upper attachment location 211b. FIGS. 35-37 show the cover 400 mounted onto the second aseptic coupling device 200.

Figure 38:
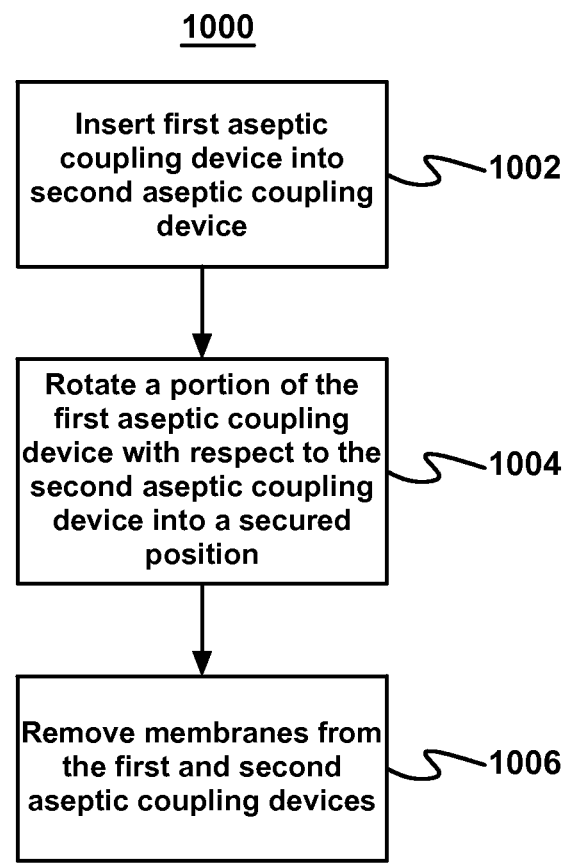
FIG. 38 is a flow diagram of a method of creating an aseptic coupling of a first coupling device and a second aseptic coupling device.

Referring now to FIG. 38, an example method 1000 for connecting aseptic coupling device 100 to aseptic coupling device 200 is shown.

First, at operation 1002, first face 118 of aseptic coupling device 100 is inserted into aseptic coupling device 200 along longitudinal axis X. During insertion, securing arms 210 are received within the locking ring 108. When front face 118 is fully inserted, ramp surfaces 218 are also received by the locking ring 108. In this position, aseptic coupling device 100 is in a pre-coupled state with respect to aseptic coupling device 200.

Next, at operation 1004, a portion of the first aseptic coupling device is rotated with respect to the second aseptic coupling device into a secured position. In one embodiment, the ramp surfaces 168, 218 are engaged by rotating the locking ring 108 with respect to the main bodies 102, 202. Once engaged, ramp surfaces 168, 218 pull aseptic coupling device 100 toward aseptic coupling device 200 to compress the sealing members 109, 209 together. As stated previously, the secured position can be obtained by rotating the ring adapter 106 until it is locked in place by the interaction of the locking feature(s) 154 and the tab(s) 136 and/or by lock members 172.

Figure 5:
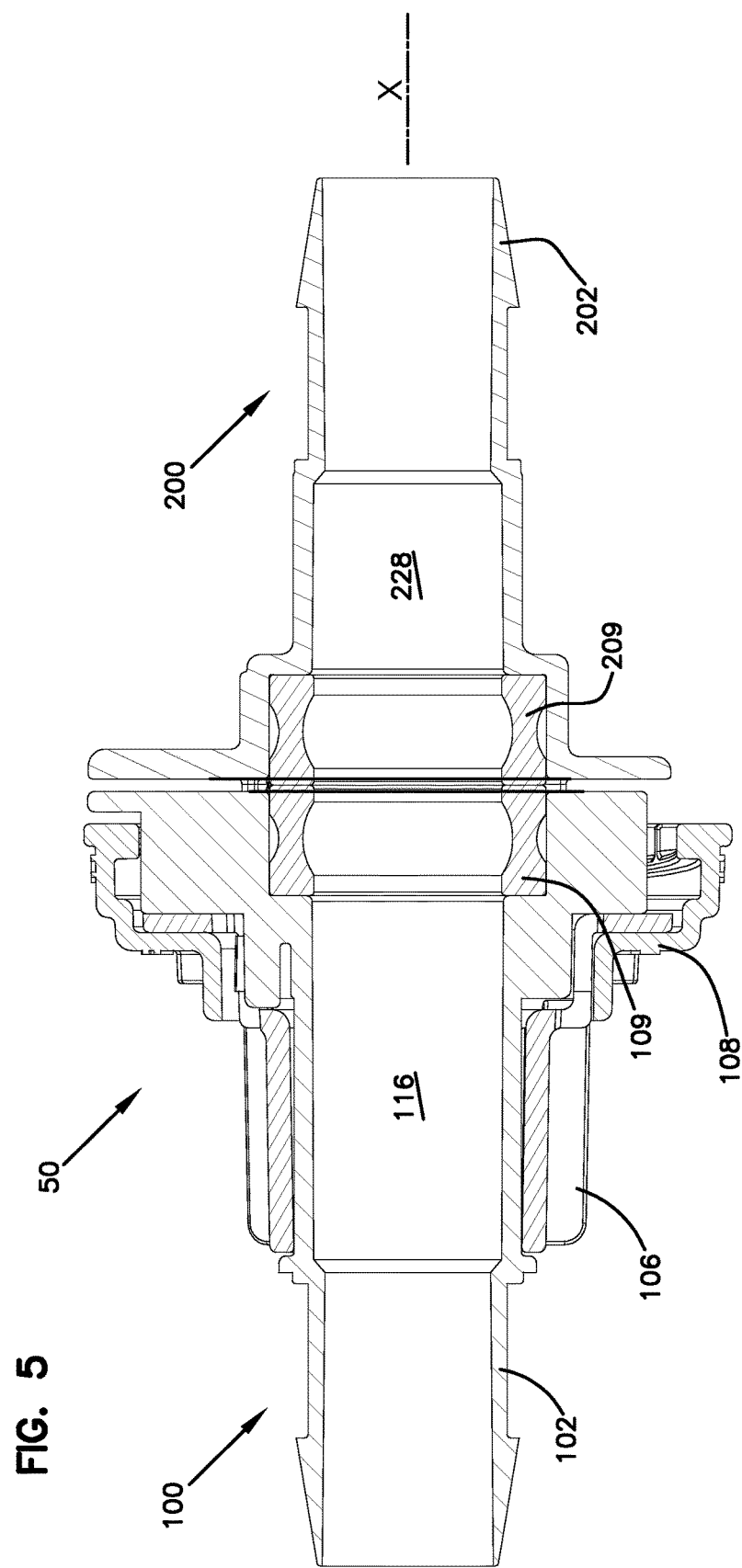
FIG. 5 is a cross-sectional view of the aseptic coupling arrangement of FIG. 2 in a coupled state.
Figure 6:
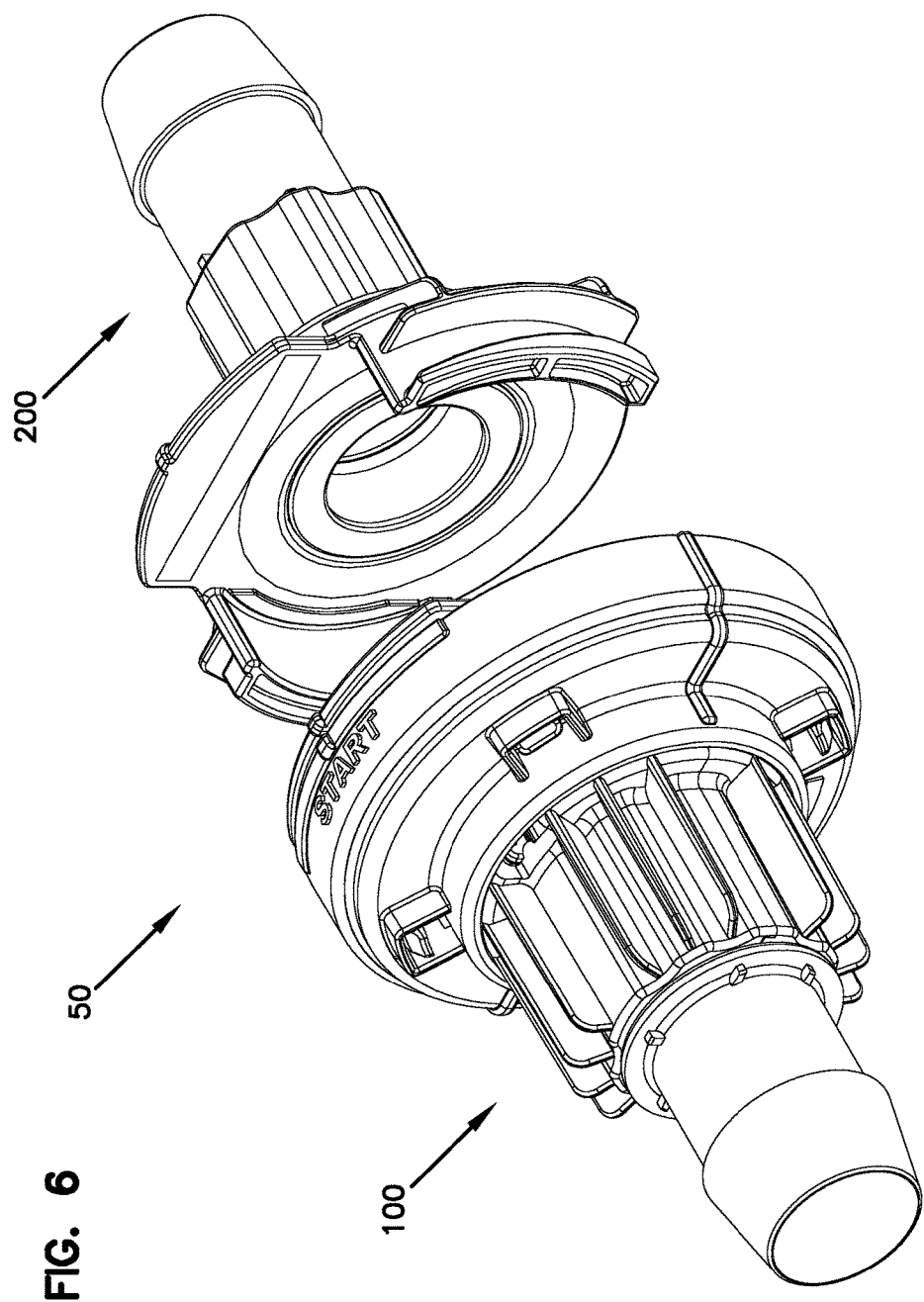
FIG. 6 is a perspective view of the aseptic coupling arrangement of FIG. 2 in an uncoupled state.
Figure 7:
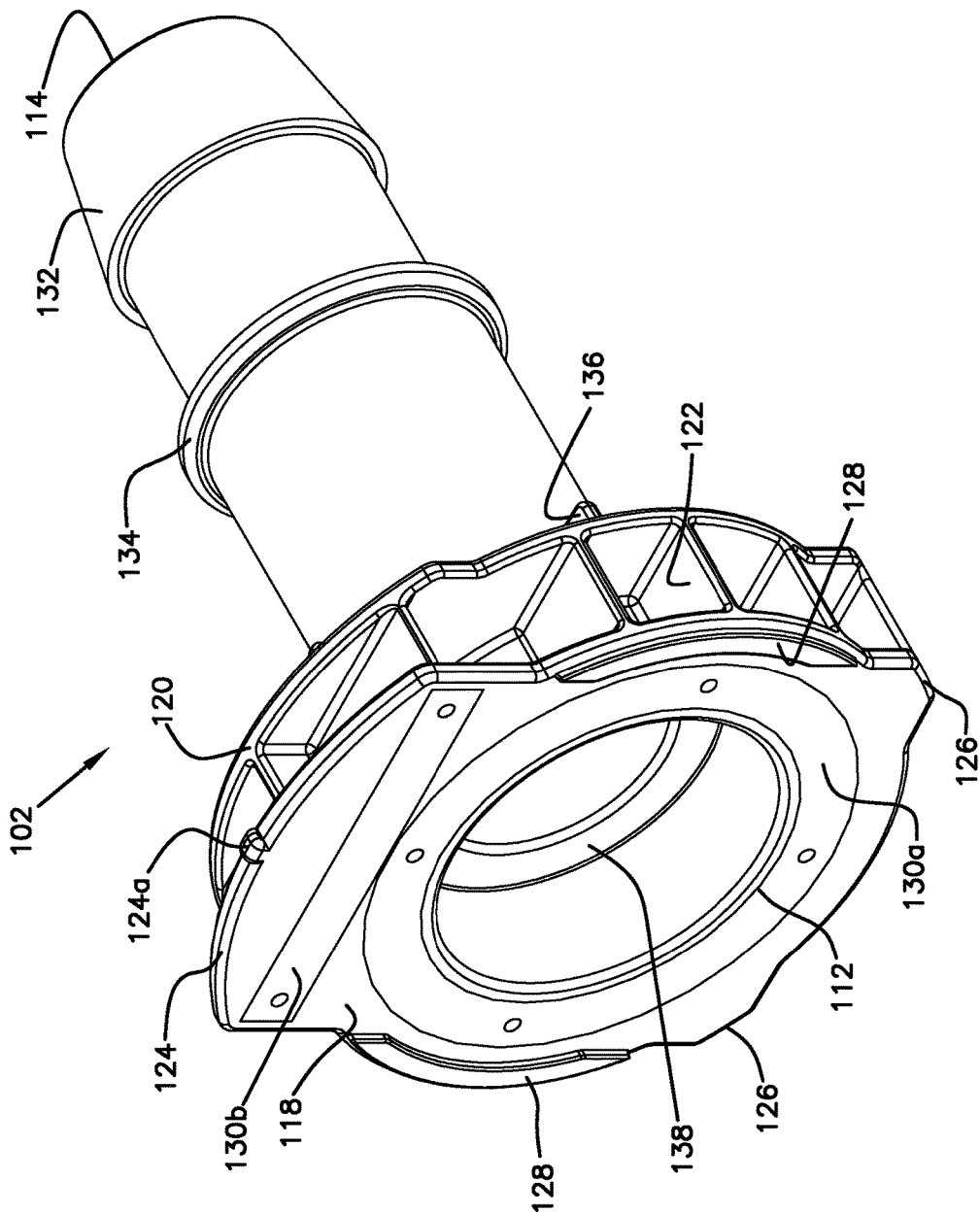
FIG. 7 is a perspective view of a main body of the male aseptic coupling of FIG. 2.
Figure 8:
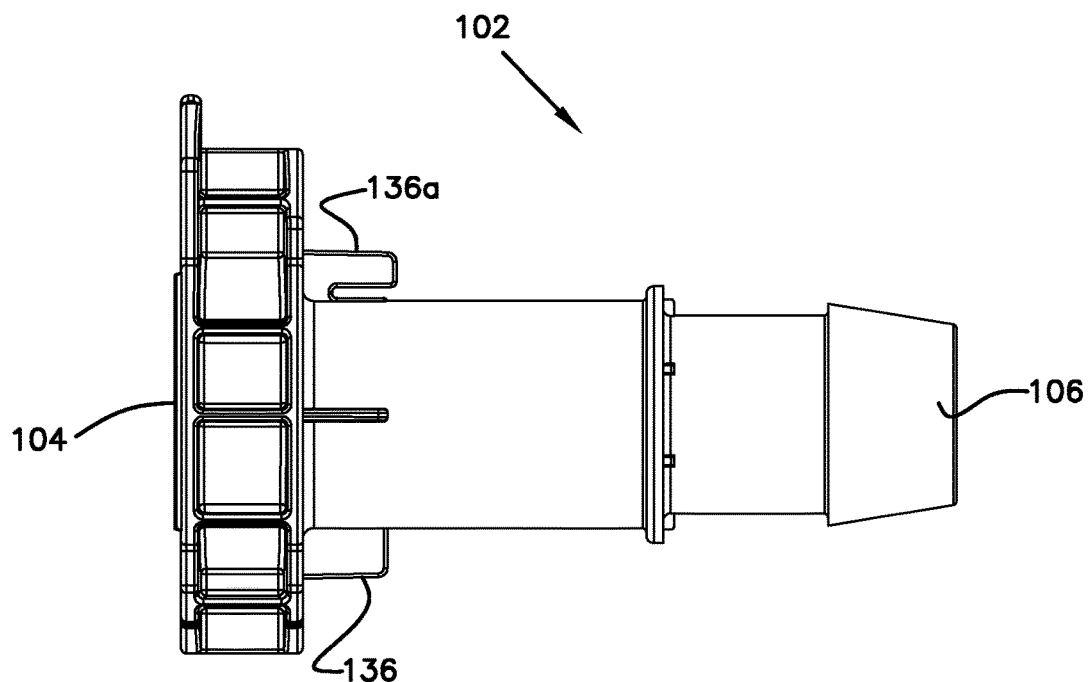
FIG. 8 is a side view of the main body of FIG. 7.
Figure 9:
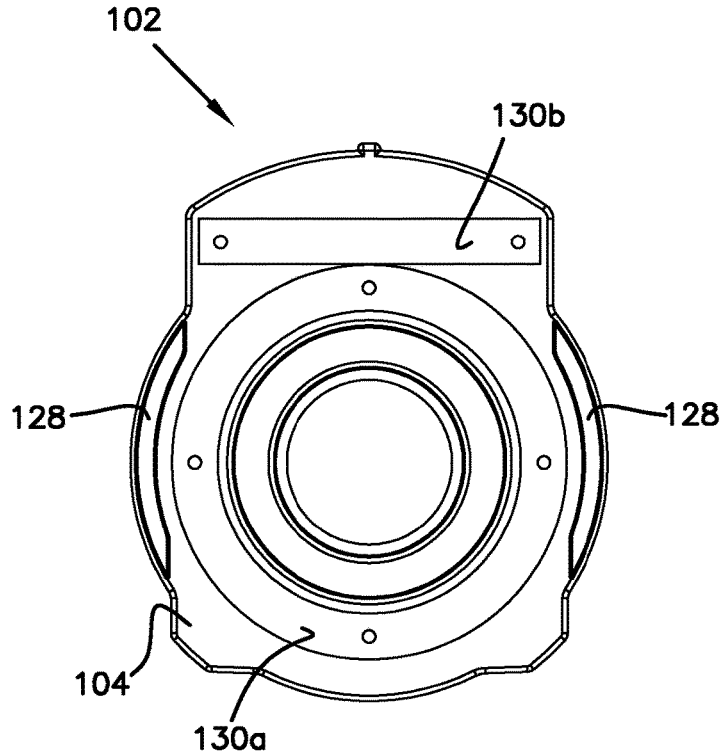
FIG. 9 is an end view of the main body of FIG. 7.
Figure 10:
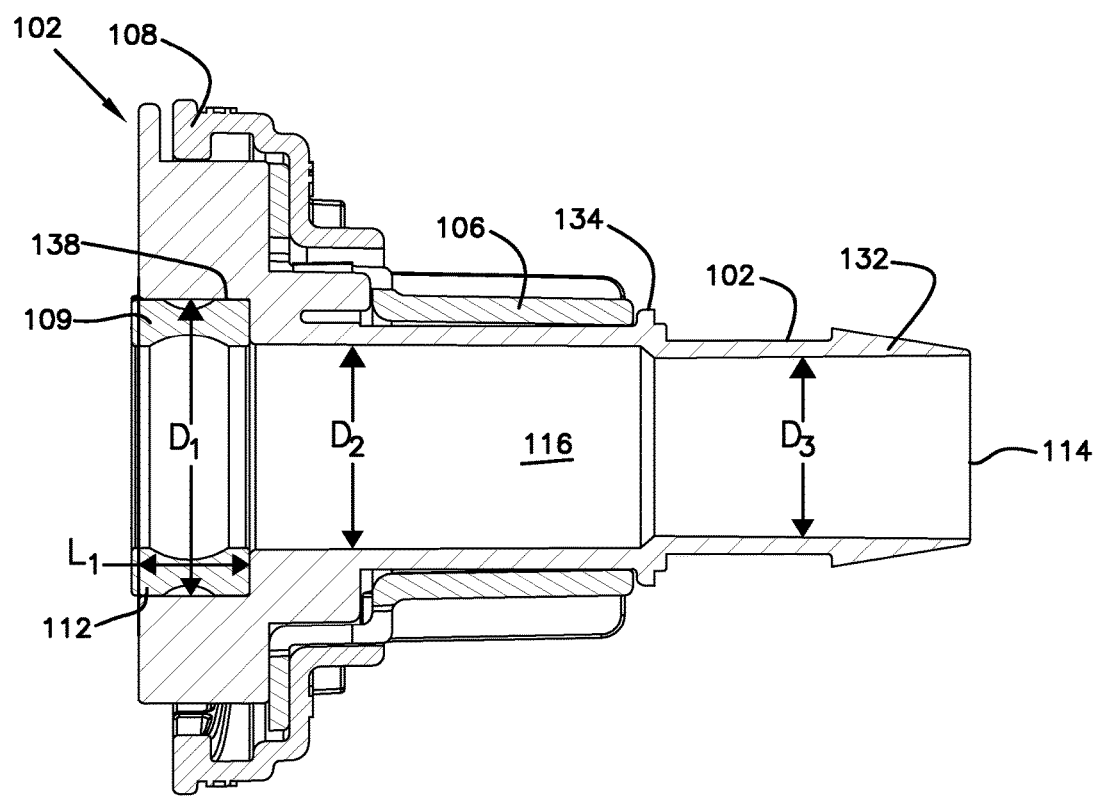
FIG. 10 is a cross-sectional view of the main body of FIG. 7.
Figure 11:
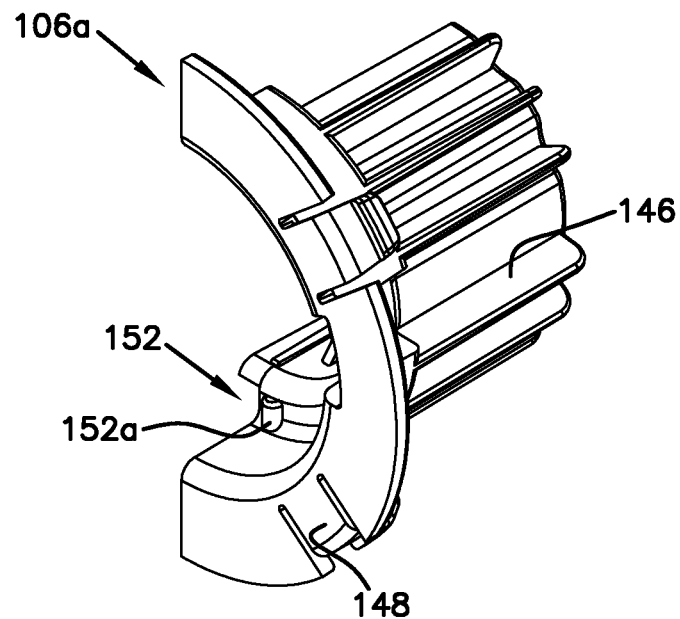
FIG. 11 is a perspective view of a ring adapter half of the male aseptic coupling of FIG. 2.
Figure 12:
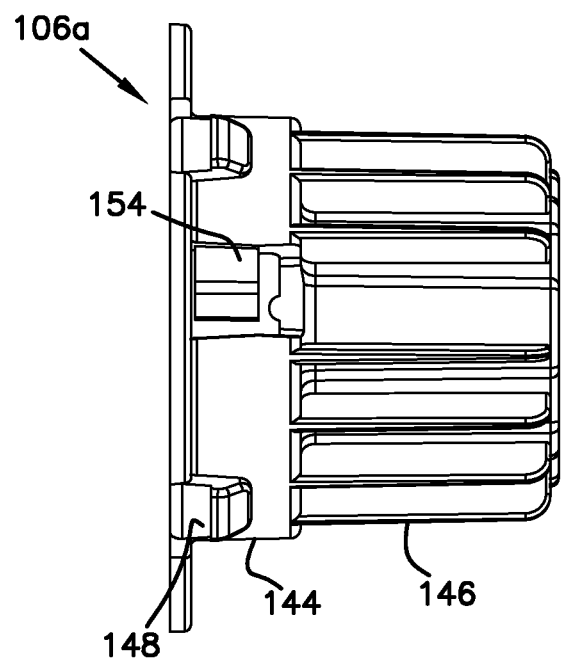
FIG. 12 is a first side view of the ring adapter half of FIG. 11.
Figure 13:
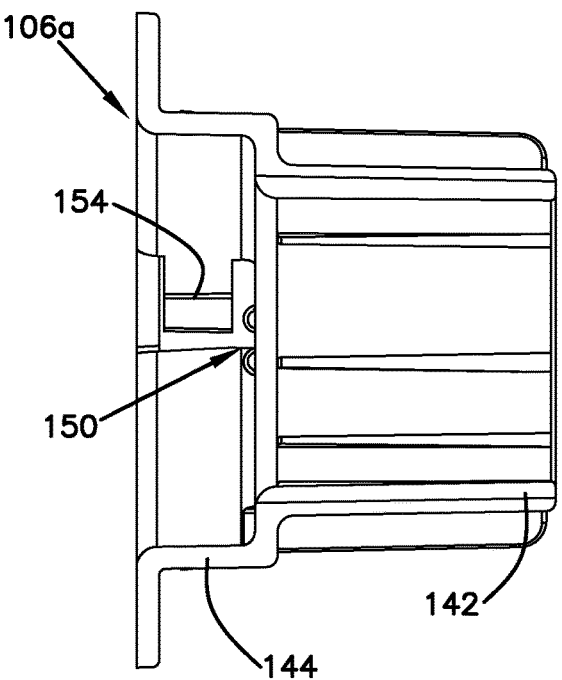
FIG. 13 is a second side view of the ring adapter half of FIG. 11.

At step 1006, membranes 104, 204 are removed from the first and second aseptic coupling devices to form a sterile connection. This step may include attaching the membrane handles 182 and 232 together and pulling them in a direction normal to and extending away from the longitudinal axis X of the aseptic coupling arrangement 50. Due to this action, membranes 104, 204 roll in on one another and are removed in a simultaneous or near simultaneous fashion. Subsequently, the sealing members 109, 209 of each of aseptic coupling devices 100, 200 engage with each other. Once this occurs, an aseptic pathway exists through passages 116, 228 of the aseptic coupling devices 100, 200. See FIG. 5. As noted above, the protrusions 128, 216 may define the level of compression for the sealing members 109, 209 where the protrusions 128, 216 are drawn into contact with each other and prevent further compression of the sealing members 109, 209. It is also noted that step 1006 may also include removing the membranes one at a time in a sequential fashion although sterility may be compromised.

Figure 39:
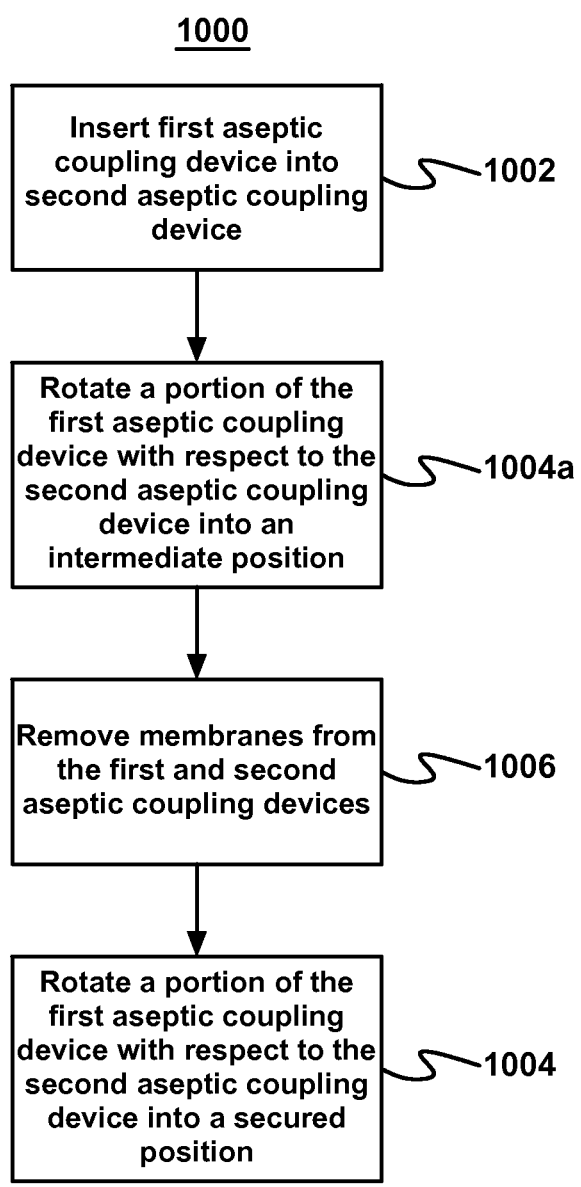
FIG. 39 is a flow diagram of a method of creating an aseptic coupling of a first coupling device and a second aseptic coupling device.
Figure 40:
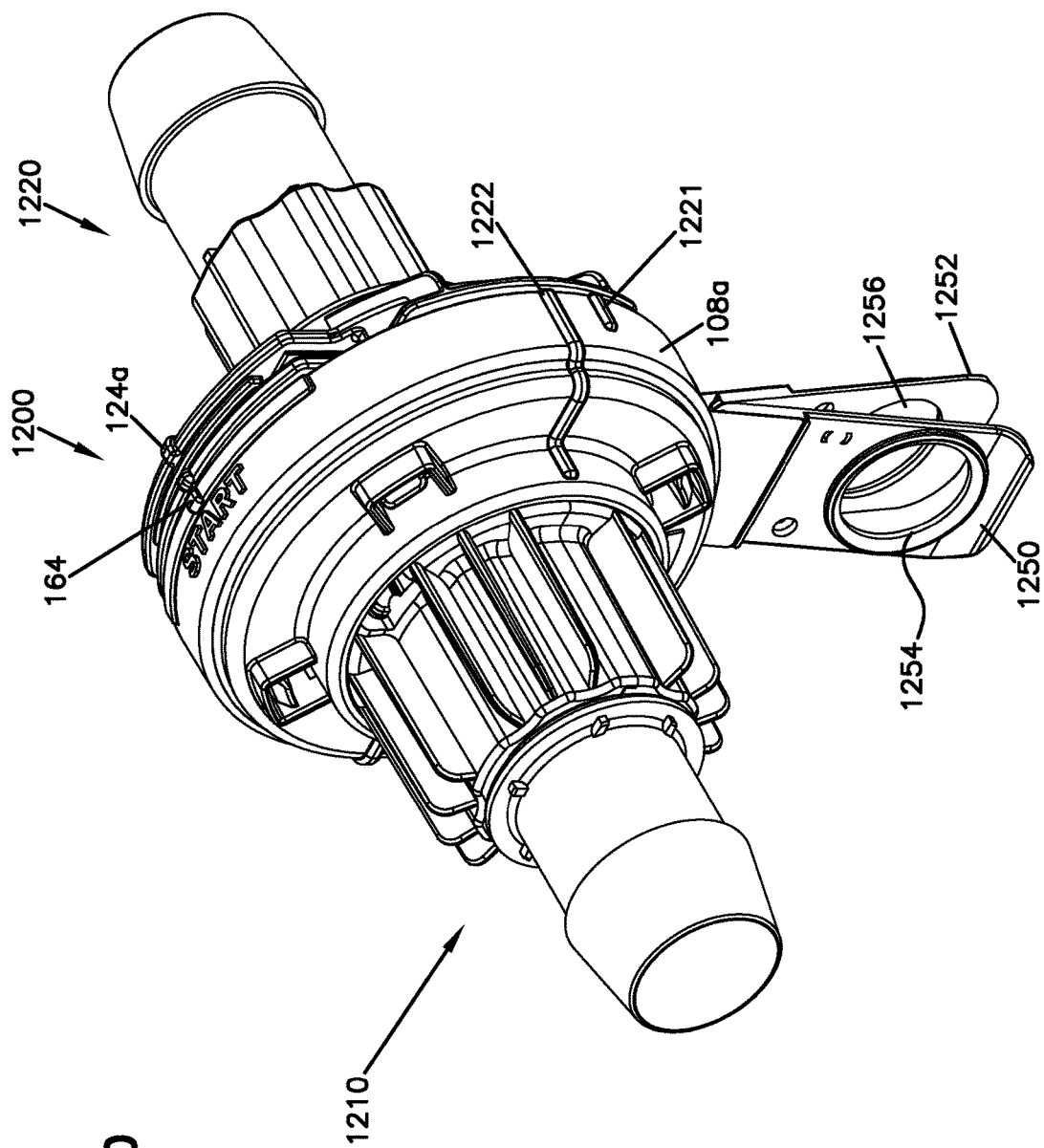
FIG. 40 is a perspective view of another example aseptic coupling arrangement in a pre-coupled state.
Figure 41:
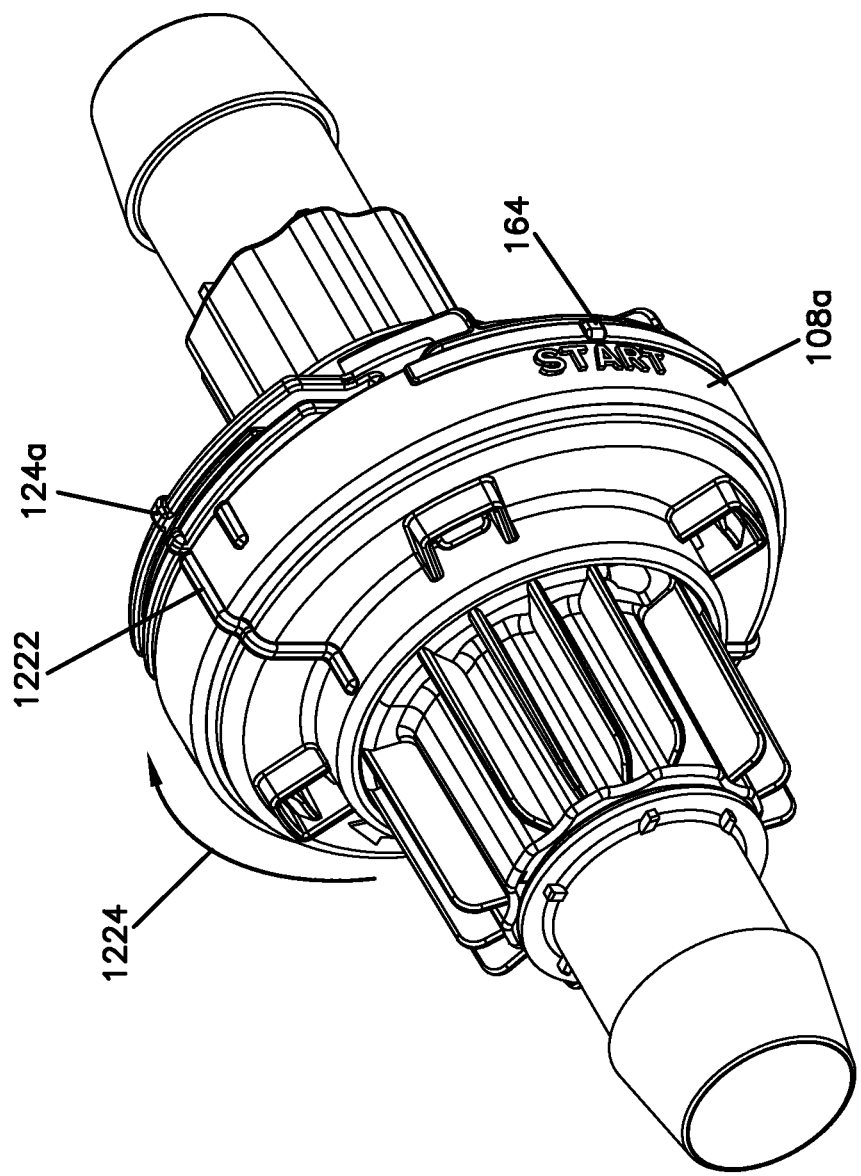
FIG. 41 is a perspective view of the aseptic coupling arrangement of FIG. 40 in a coupled state.
Figure 42:
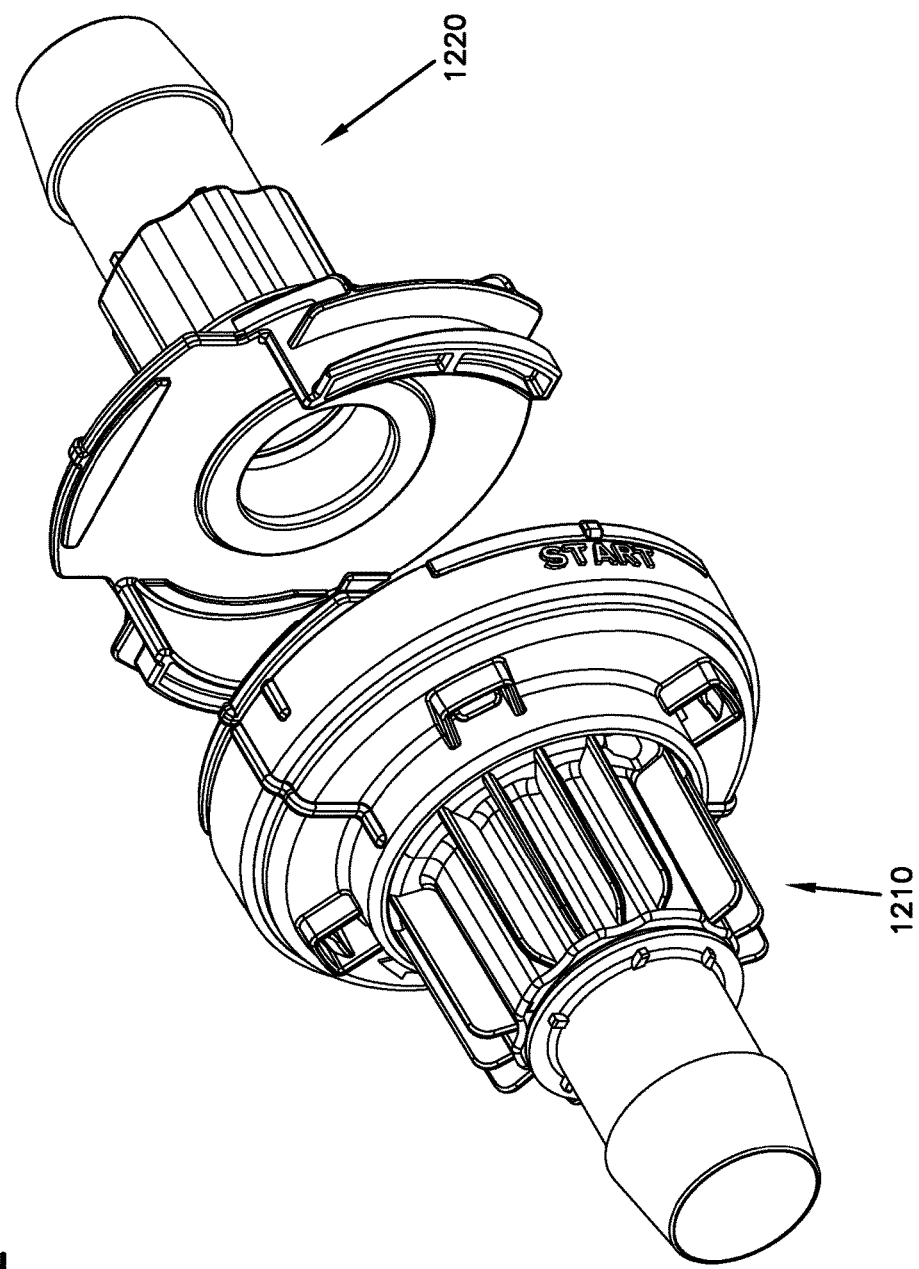
FIG. 42 is a perspective view of the aseptic coupling arrangement of FIG. 40 in an uncoupled state.

With reference to FIG. 39, process 1000 is shown with an additional step 1004a. In step 1004a, a portion of the first aseptic coupling device, such as the lock ring 108 and/or the ring adapter 106, is rotated with respect to the second aseptic coupling device into an intermediate position. The intermediate position may be a secured position in which reverse rotation is not possible or a non-secured position in which reverse rotation may occur. The intermediate position is a position in which the seals 109, 209 are compressed sufficiently to form a seal with each other, but not compressed such that the membranes 104, 204 cannot be removed. Where an intermediate position is utilized, the secured position of step 1004 may be of greater compressive force than that applied in the intermediate step 1004a. In one embodiment, the compressive force in the secured position is of a magnitude that the membranes 102, 204 could not be removed with such a force present.

Referring now to FIGS. 40-48, another example aseptic coupling arrangement 1200 including a first aseptic coupling device 1210 and a second aseptic coupling device 1220 is shown. The aseptic coupling arrangement 1200 is similar to the aseptic coupling arrangement 50 described above, with the following noted exceptions.

A lock ring 108a of the first aseptic coupling device 1210 includes the indicia 164 illustrating the rotational start position of the lock ring 108a during coupling of the first aseptic coupling device 1210 to the second aseptic coupling device 1220. The indicia 164 lines up with the alignment protrusion 124a on the second aseptic coupling device 1220.

The lock ring 108a also includes indicia 1221 and 1222 formed on opposing sides of the lock ring 108a. When the lock ring 108a is rotated clockwise (i.e., direction 1224) to the pre-coupled state, the indicia 1221 lines up with the alignment protrusion 124a to provide a visual indication of the pre-coupled state. An audible indication can also be provided.

Further, when the lock ring 108a is further rotated in the direction 1224 to the coupled state, the indicia 1222 lines up with the alignment protrusion 124a to provide a visual indication of the coupled state. See FIG. 41. An audible indication can also be provided.

The aseptic coupling arrangement 1200 also includes handles 1250, 1252 that are connected to each other in a manner similar to that described above for handles 182, 232. Once attached, a single handle is formed that can be pulled by an operator with the assurance that the membranes 104, 204 will be removed in simultaneous or near simultaneous fashion. In this example, each of the handles 1250, 1252 forms an aperture 1254, 1256, respectively. The user can place a finger or other instrument through the apertures 1254, 1256 to aid in applying the consistent force necessary to pull the membranes 104, 204.

Figure 43:
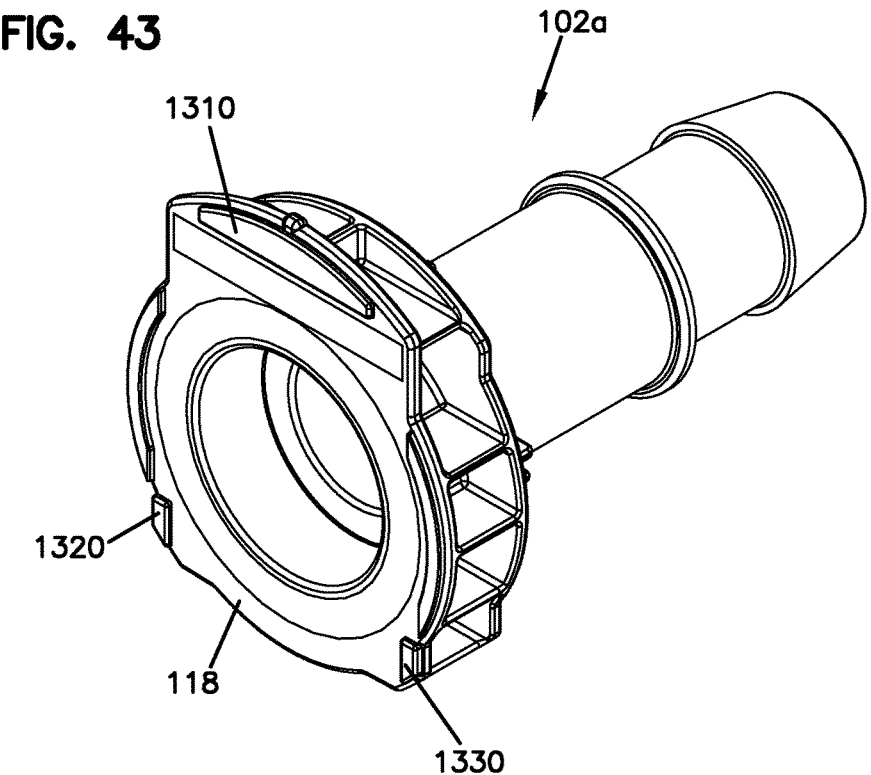
FIG. 43 is a perspective view of a main body of the male aseptic coupling of FIG. 40.
Figure 44:
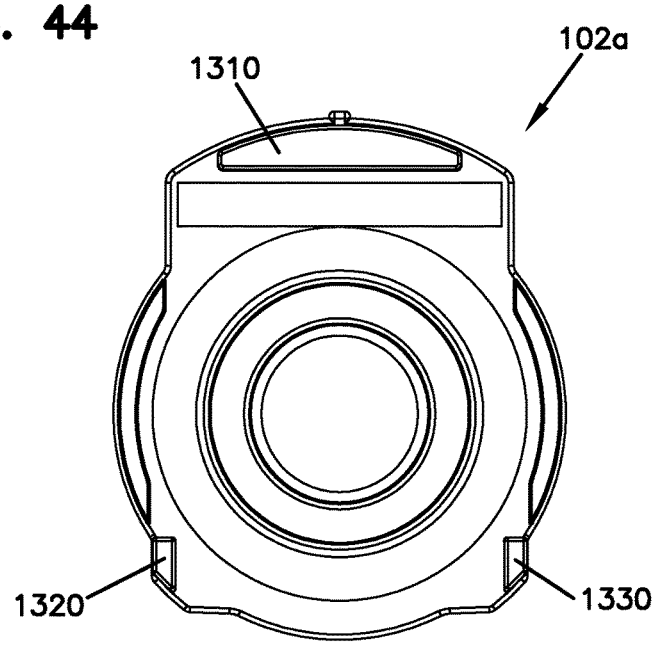
FIG. 44 is a front view of the main body of FIG. 43.
Figure 45:
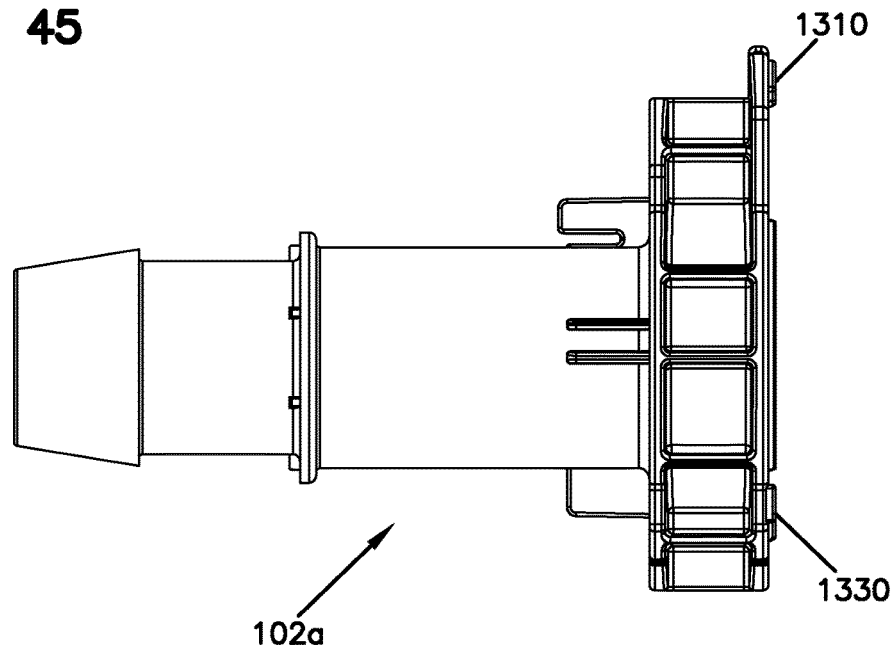
FIG. 45 is a side view of the main body of FIG. 43.
Figure 46:
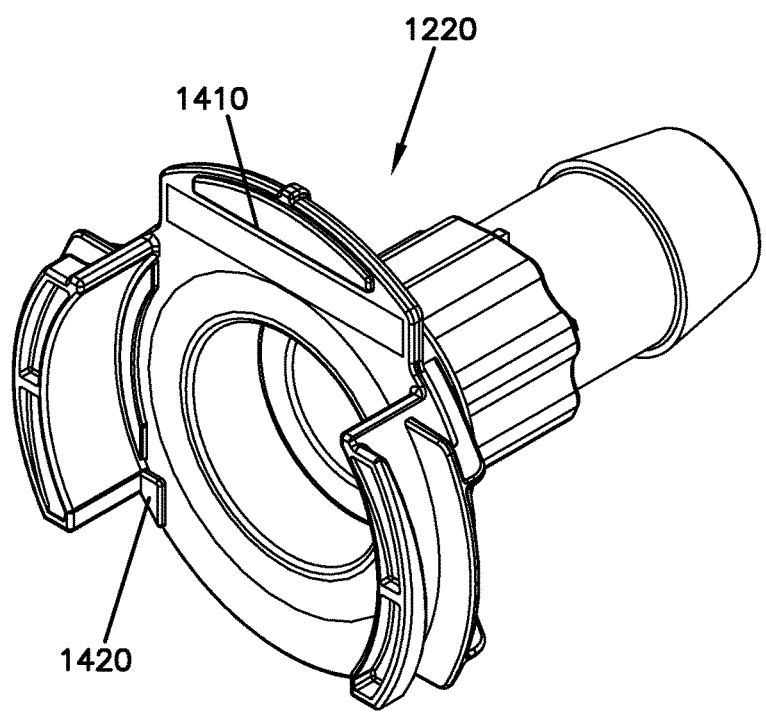
FIG. 46 is a perspective view of the female aseptic coupling of FIG. 40.
Figure 47:
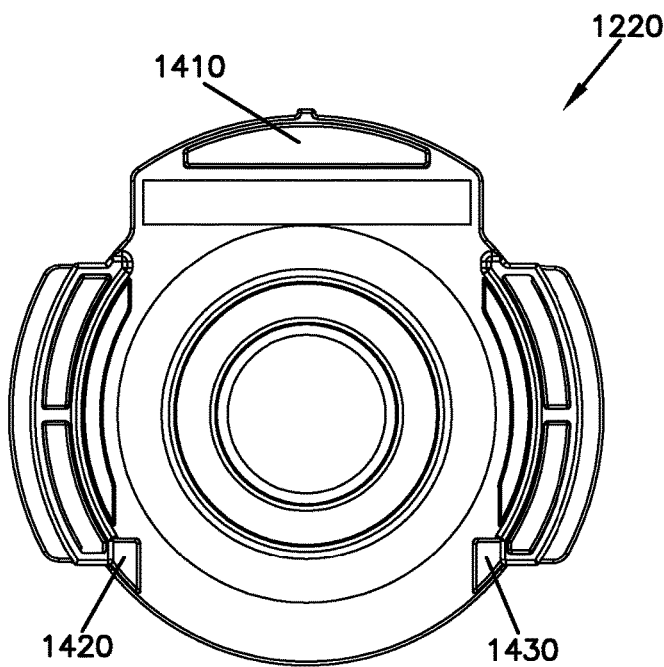
FIG. 47 is a front view of the female aseptic coupling of FIG. 46.
Figure 48:
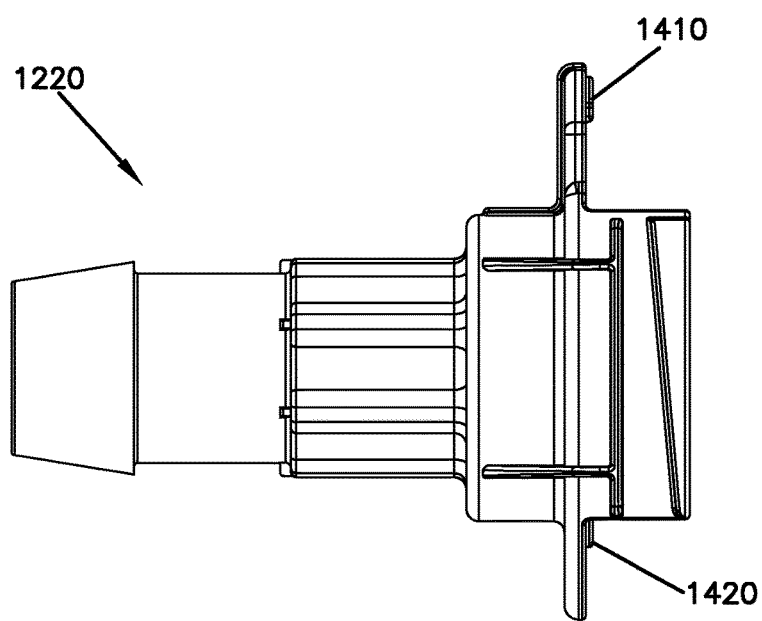
FIG. 48 is a side view of the female aseptic coupling of FIG. 46.
Figure 49:
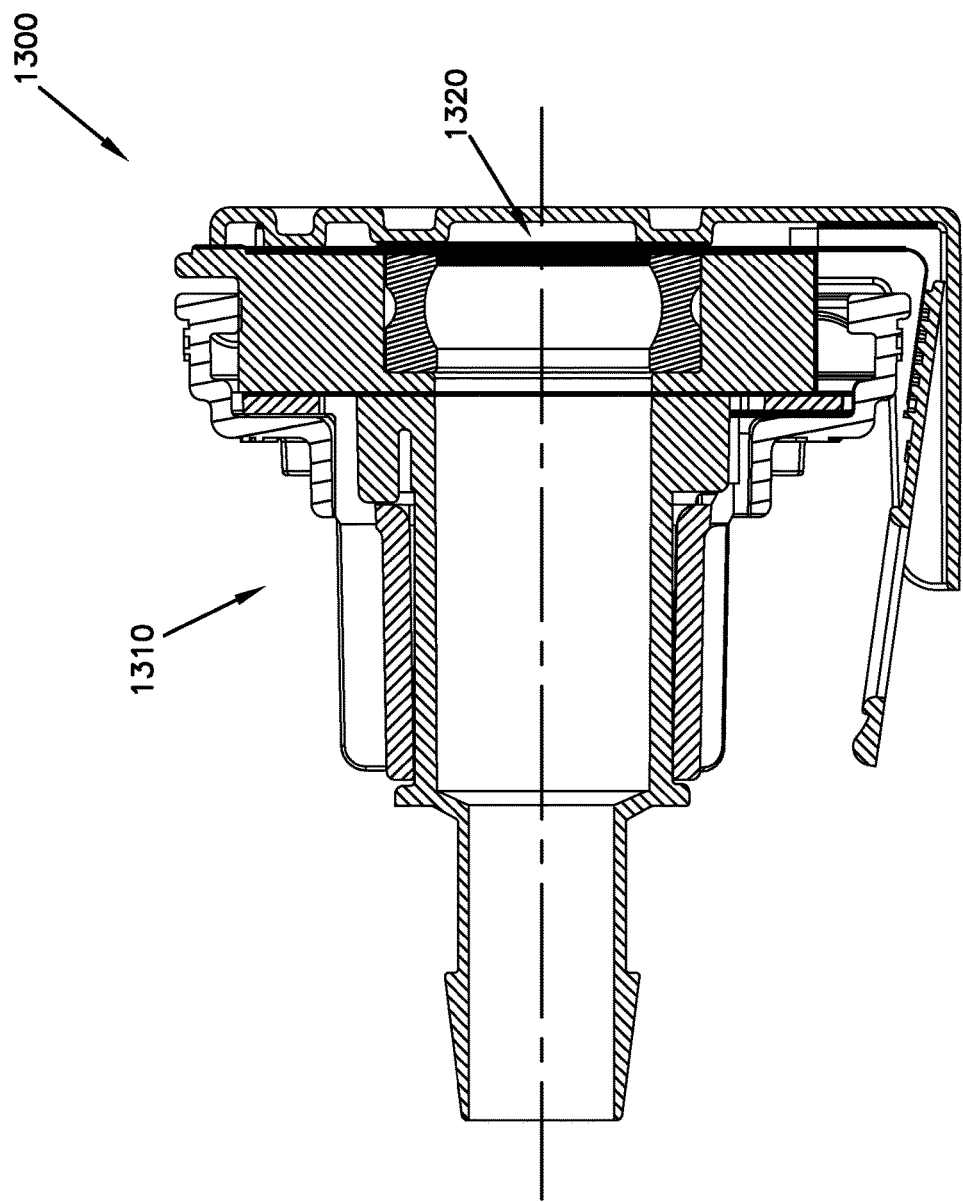
FIG. 49 is a side cross sectional view of another example aseptic coupling device.

Referring to FIGS. 43-45, the first face 118 of a main body 102a of the first aseptic coupling device 1210 includes protrusions 1310, 1320, 1330 formed on the first face 118. These protrusions 1310, 1320, 1330 are positioned to engage corresponding protrusions 1410, 1420, 1430 on a first face of the second aseptic coupling device 1220. See FIGS. 46-48. A height of the protrusions 1301, 1320, 1330 and the protrusions 1410, 1420, 1430 is sized so that there is a slight gap between the protrusions 1301, 1320, 1330 and the protrusions 1410, 1420, 1430 when the aseptic coupling arrangement 1200 is in the pre-coupled state, and an even smaller gap therebetween when in the coupled state. However, if any torque is applied to one or both of the first aseptic coupling device 1210 and the second aseptic coupling device 1220, one or more of the protrusions 1301, 1320, 1330 engage the protrusions 1410, 1420, 1430 to limit any rocking of the devices 1210, 1220 relative to one another.

In some of the examples provided herein, the aseptic coupling devices are coupled to one another and form a secure, sterile connection without requiring additional components to be added to make the connection. For example, the aseptic coupling devices are coupled to one another without using external components to secure the connection. Such external components include secondary clamps.

In example embodiments, the aseptic coupling devices and their respective covers are made of a polymeric material. For example, in one embodiment, the aseptic coupling devices are made of polycarbonate and the sealing members used therein are made of a silicone rubber. Other materials can be used.

In some embodiments, membranes 104, 204 are autoclavable and gamma stable for sterilization. In various embodiments, membranes 104, 204 are a composite design that consists of two components: 1 tag and 1 vent. The tag is a laminate including: a polyethylene terephthalate (PET) film, polyethylene (PE) foam, aluminum foil, and a sealing layer. The foam and/or foil may or may not exist in the final configuration. The sealing layer allows the tag to be bonded or welded to polycarbonate connectors (e.g., aseptic coupling devices 100 and 200).

The vent is an expanded polytetrafluoroethylene (ePTFE) membrane that will be bonded or welded onto the tag. Membranes 104, 204 are located over the center of the flow area of aseptic coupling devices 100 and 200, respectively, when the tags and vents are bonded or welded to connectors. The vent allows air and steam to flow into the system 10 during sterilization. The pore size of membranes 104, 204 are such that membranes 104, 204 filter out microorganisms larger than 0.2 microns.

In another embodiment, membranes 104, 204 are a polyethersulfone (PES) and polyester laminate membrane. This membrane is hydrophobic and breathable. The pore size is such that microorganisms larger than 0.2 microns are filtered out. When bonded, the polycarbonate melts into the polyester fibers, so that the PES acts as the filter, and the polyester acts as the structure.

In other embodiments, membranes 104, 204 are a Tyvek® membrane (from DuPont) that is coated on one side to allow membranes 104, 204 to be bonded to polycarbonate connectors (e.g., aseptic coupling devices 100 and 200). Tyvek® is breathable in nature, so there is no need for an additional vent. Tyvek® is a non-woven polyethylene membrane.

Referring now to FIGS. 49-53, another example aseptic coupling arrangement 1300 is shown including a first aseptic coupling device 1310 and a second aseptic coupling device 1311. The aseptic coupling arrangement 1300 is similar to the other aseptic coupling arrangements described herein, with the following noted exceptions.

Figure 50:
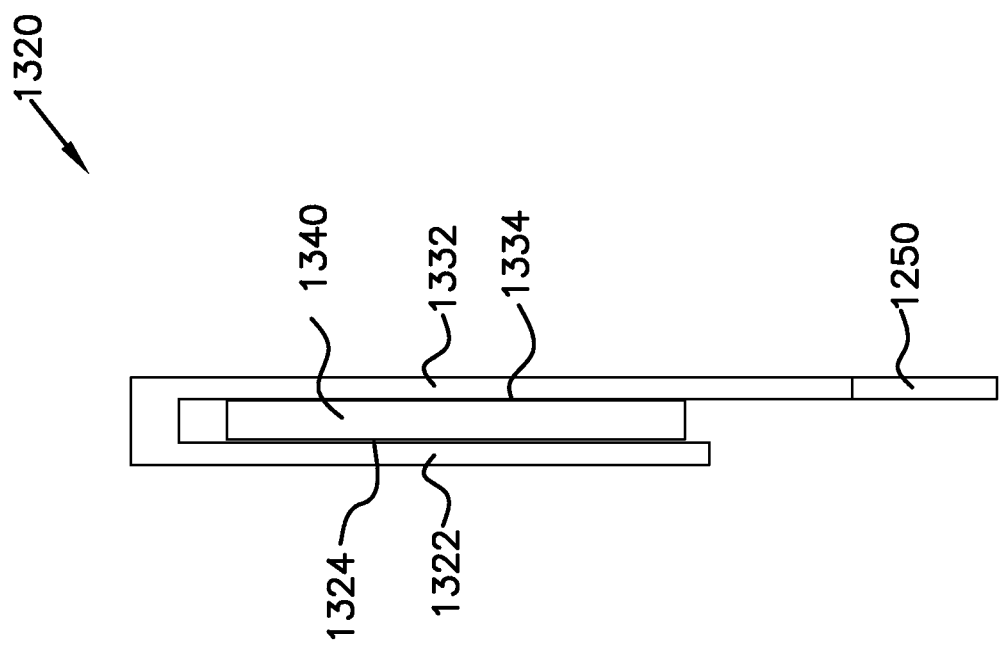
FIG. 50 is a plan view of a membrane of the aseptic coupling device of FIG. 49.

The first aseptic coupling device 1310 includes a membrane 1320. The membrane 1320 is similar to the membranes 104, 204 described above. However, as shown in FIG. 50, the membrane 1320 includes a low friction member 1340 positioned between a first portion 1322 and a second portion 1332 of the membrane 1320. The first portion 1322 is coupled to the front face of the first aseptic coupling device 1310. The second portion 1324 is the portion of the membrane 1320 that is folded back upon the first portion 1322 and that extends out of the first aseptic coupling device 1310 and terminates at the handle 1250.

Figure 51:
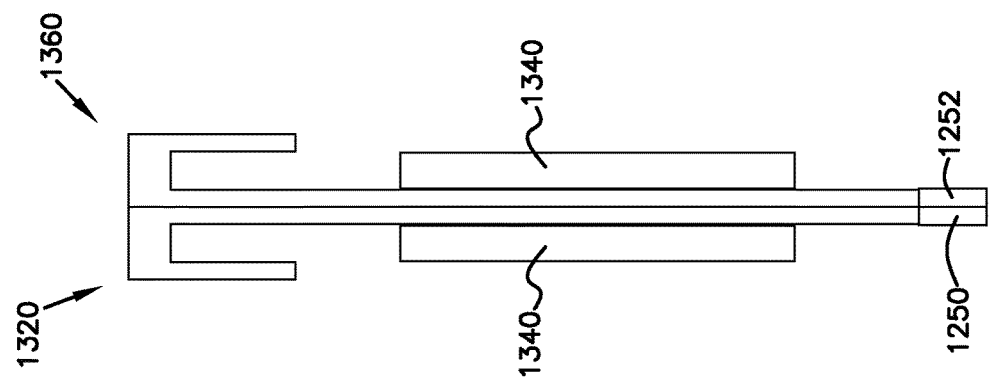
FIG. 51 is a plan view of membranes of an aseptic coupling arrangement including the aseptic coupling device of FIG. 49.

In this example, the low friction member 1340 is coupled to a surface 1334 of the second portion 1324. As shown in FIG. 51 (which also illustrates the mating membrane 1360 of the second aseptic coupling device 1311 configured in an identical, mirrored arrangement), as the second portion 1324 is pulled, the low friction member 1340 rides along a surface 1324 of the first portion 1322. The low friction member 1340 decreases the friction between the surfaces 1324, 1334 so that the membrane 1320 can more easily be pulled out. Further, since the low friction member 1340 is coupled to the second portion 1324, it is not necessary for the low friction member 1340 to be folded as the membrane 1320 is removed.

Figure 52:
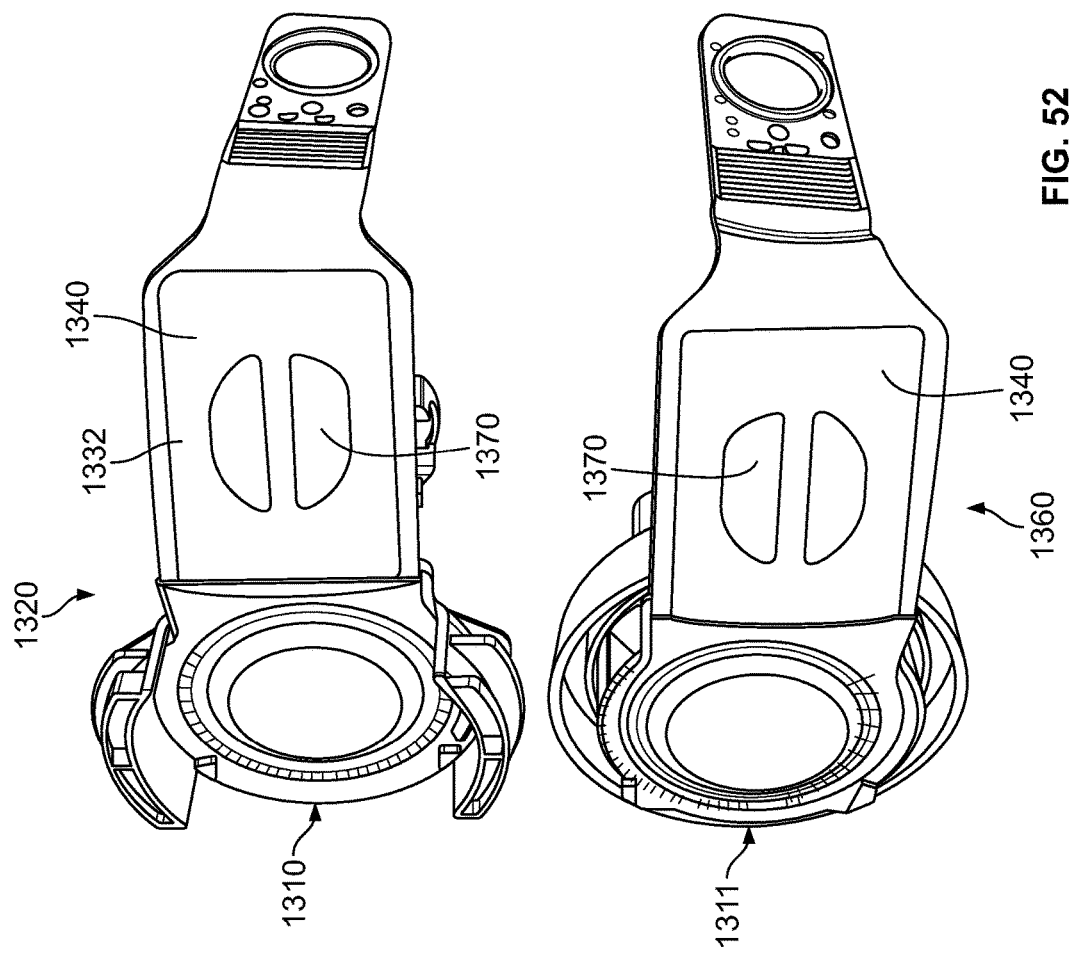
FIG. 52 is a front view of the aseptic coupling arrangement of FIG. 51.

Referring now to FIG. 52, the first aseptic coupling device 1310 and the second aseptic coupling device 1311 are shown with the membranes 1320, 1360 folded open to show the low friction members 1340 positioned thereon. In these examples, the low friction members 1340 include adhesive to allow the low friction members 1340 to adhere to the surface 1334 of the membranes 1320, 1360.

Figure 53:
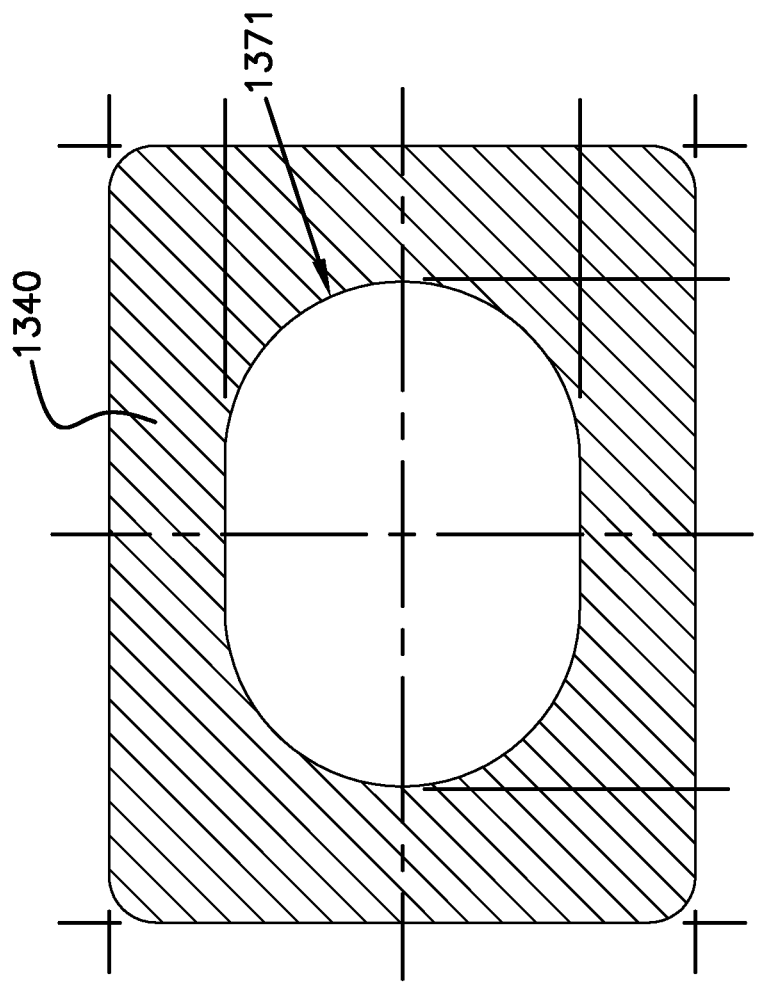
FIG. 53 is a plan view of an alternative low friction member.

In addition, in this example, each of the low friction members 1340 includes an aperture 1370 formed therein. This aperture 1370 allows the first and second aseptic coupling devices 1310, 1311 to be sterilized during manufacture. For example, once the membranes 1320, 1360 are in place, sterilization techniques such as autoclaving can be used. The apertures 1370 allow for the autoclaving (i.e., steam penetration) of the first and second aseptic coupling devices 1310, 1311 through the apertures 1370. In FIG. 53, an aperture 1371 of a different shape is formed in the low friction member 1340. Other configurations are possible.

The low friction member 1340 is made of a material with a lower coefficient of friction than the membranes 1320, 1360. In this example, the membranes 1320, 1360 are made of PES, and the low friction member 1340 is made of PTFE. In such an example, the pullout force required was reduced approximately 40 percent over use of the membranes without the low friction member. Other low friction materials, such as smooth plastics or metals, can be used.

In example embodiments, the low friction member, in the form depicted herein or in revised form, can be used in such applications as the aseptic coupling devices described in U.S. patent application Ser. No. 12/724,125 filed on Mar. 15, 2010, U.S. patent application Ser. No. 13/768,340 filed on Feb. 15, 2013, and U.S. patent application Ser. No. 13/800,630 filed on Mar. 13, 2013, the entireties of all of these applications being hereby incorporated by reference.

The various embodiments described above are provided by way of illustration only and should not be construed to limit the claims attached hereto. Those skilled in the art will readily recognize various modifications and changes that may be made without following the example embodiments and applications illustrated and described herein, and without departing from the true spirit and scope of the disclosure.

What is claimed is:

1. An aseptic coupling device, comprising:
a main coupling body having a front face that defines an opening;
a membrane including a first portion and an adjacent second portion, wherein the first and second portions are formed from a material having a first coefficient of friction, wherein the first portion is attached directly to the front face completely around the opening to thereby cover the opening, and wherein the second portion is folded over on the first portion; and
a low friction member being formed from a material having a second coefficient of friction that is lower than the first coefficient of friction, the low friction member being positioned between the first and second portions of the membrane and attached to the second portion;
wherein the low friction member defines an aperture void of the low friction member;
wherein the second portion of the membrane covers the aperture; and
wherein the aperture is positioned to allow for sterilization of the aseptic coupling device through the aperture and the second portion of the membrane.

2. The aseptic coupling device of claim 1, wherein the low friction member is made of polytetrafluoroethylene.

3. The aseptic coupling device of claim 1, wherein the membrane includes a single fold.

4. The aseptic coupling device of claim 3, wherein the single fold is between the first portion and the second portion.

5. The aseptic coupling device of claim 1, wherein it is not necessary for the low friction member to be folded as the membrane is removed from the main coupling body.

6. The aseptic coupling device of claim 1, wherein a circular portion of the first portion of the membrane is attached directly to the front face completely around the opening and a second attachment portion of the membrane is also attached directly to the front face.

7. The aseptic coupling device of claim 6, wherein the second attachment portion of the membrane is a rectangular portion.

8. The aseptic coupling device of claim 1, further comprising a cover releasably coupleable with the main coupling body, wherein while the cover is coupled with the main coupling body the cover presses the membrane against the front face of the main coupling body.

9. The aseptic coupling device of claim 1, wherein an entirety of the membrane is separated from the main coupling body when the aseptic coupling device is in use.

10. A membrane for an aseptic coupling device, the membrane comprising:
a first portion configured to be attached directly to a front face of the aseptic coupling device completely around an opening defined by the front face to thereby cover the opening;

a second portion adjacent the first portion and folded over on the first portion, wherein the first and second portions are formed from a material having a first coefficient of friction; and a low friction member positioned between the first and second portions of the membrane, the low friction member being formed from a material having a second coefficient of friction that is lower than the first coefficient of friction, wherein the low friction member defines an aperture void of the low friction member, and wherein the aperture is positioned to allow sterilization of the aseptic coupling device therethrough;

wherein the low friction member is attached to the second portion such that the low friction member rides along a surface of the first portion as the membrane is removed from the aseptic coupling device.

11. The membrane of claim 10, wherein the low friction member is made of polytetrafluoroethylene.

12. The membrane of claim 10, wherein the membrane includes a single fold, and wherein the single fold is located between the first portion and the second portion.

13. The membrane of claim 10, wherein it is not necessary for the low friction member to be folded as the membrane is removed from the aseptic coupling device.

14. A method for forming an aseptic coupling device, the method comprising:

forming an aperture through a low friction member;

providing a membrane having a first portion and an adjacent second portion;

coupling the low friction member to the membrane second portion and folding the membrane first portion over the low friction member and first portion;

coupling the membrane to a front face of an aseptic coupling device that defines an opening, wherein the first portion is attached directly to the front face completely around the opening to thereby cover the opening; and sterilizing the aseptic coupling device through the aperture.

15. The method of claim 14, wherein the low friction member is made of polytetrafluoroethylene.

16. The method of claim 14, wherein the membrane includes a single fold, and wherein the single fold is located between the first portion and the second portion.

17. The method of claim 14, wherein a circular portion of the first portion of the membrane is attached directly to the front face completely around the opening and a second rectangular portion of the membrane is also attached directly to the front face.

18. The method of claim 14, further comprising releasably coupling a cover with the aseptic coupling device, and wherein while the cover is coupled with the aseptic coupling device the cover presses the membrane against the front face of the aseptic coupling device.

19. The method of claim 14, wherein it is not necessary for the low friction member to be folded as the membrane is removed from the aseptic coupling device.

* * * * *